United States Patent
Agüeros Bazo et al.

(10) Patent No.: US 9,522,197 B2
(45) Date of Patent: Dec. 20, 2016

(54) NANOPARTICLES COMPRISING A CYCLODEXTRIN AND A BIOLOGICALLY ACTIVE MOLECULE AND USES THEREOF

(75) Inventors: Maite Agüeros Bazo, Pamplona-Navarra (ES); Hesham H. A. Salman, Pamplona-Navarra (ES); Juan Manuel Irache Garreta, Pamplona-Navarra (ES); Miguel Angel Campanero Martínez, Pamplona-Navarro (ES)

(73) Assignee: INNOUP FARMA, S.L., Navarra (ES)

( * ) Notice: Subject to any disclaimer, the term of this patent is extended or adjusted under 35 U.S.C. 154(b) by 209 days.

(21) Appl. No.: 12/596,664

(22) PCT Filed: Apr. 18, 2008

(86) PCT No.: PCT/ES2008/000269
§ 371 (c)(1),
(2), (4) Date: Dec. 3, 2009

(87) PCT Pub. No.: WO2008/129106
PCT Pub. Date: Oct. 30, 2008

(65) Prior Publication Data
US 2010/0136129 A1    Jun. 3, 2010

(30) Foreign Application Priority Data

Apr. 20, 2007   (ES) .................... 200701074

(51) Int. Cl.
| | |
|---|---|
| A61K 9/50 | (2006.01) |
| A61K 47/48 | (2006.01) |
| A61K 9/00 | (2006.01) |
| A61K 9/51 | (2006.01) |
| B82Y 5/00 | (2011.01) |
| A61K 9/14 | (2006.01) |

(52) U.S. Cl.
CPC ....... A61K 47/48969 (2013.01); A61K 9/0065 (2013.01); A61K 9/5138 (2013.01); A61K 9/5161 (2013.01); B82Y 5/00 (2013.01); A61K 9/14 (2013.01); A61K 9/141 (2013.01); A61K 9/145 (2013.01); A61K 9/146 (2013.01)

(58) Field of Classification Search
None
See application file for complete search history.

(56) References Cited

U.S. PATENT DOCUMENTS

| | | | |
|---|---|---|---|
| 6,284,746 B1 * | 9/2001 | Szente .................. | A61K 31/335 514/58 |
| 6,881,421 B1 * | 4/2005 | da Silveira et al. .......... | 424/489 |
| 2005/0009783 A1 | 1/2005 | Kagkadis | |
| 2005/0043481 A1 | 2/2005 | Gref et al. | |
| 2008/0220030 A1 | 9/2008 | Alonso Fernandez et al. | |

FOREIGN PATENT DOCUMENTS

| | | |
|---|---|---|
| EP | 1369110 A1 | 3/2002 |
| EP | 1752142 A2 | 2/2007 |
| WO | 0241829 A2 | 5/2002 |

OTHER PUBLICATIONS

Hamada et al. "Enhancement of water-solubility and bioactivity of Paclitaxel using modified cyclodextrins" 2006, Journal of Bioscience and Bioengineering, vol. 102, pp. 369-371.*
Singh et al. "Biotechnological applications of cyclodextrins", 2002, Biotechnology Advances, vol. 20, pp. 341-359.*
Fushiki et al. "Evaluation of Paclitaxel against Human Adenocarcinoma of the Uterine Cervix in Nude Mice", International Journal of Clinical Oncology Sep. 1997, vol. 2, Issue 3, pp. 152-155.*
http://en.wikipedia.org/wiki/P-glycoprotein, printed from web Mar. 17, 2014.*
http://beta.merriam-webster.com/dictionary/derivative, retrieved on Dec. 9, 2015.*
Arbos et al., Gantrez an as a new polymer for the preparation of ligand-nanoparticle conjugates, Journal of Controlled Release 83 (2002) 321-330.*
M. Agueros, et al., Simultaneous quantification of different cyclodextrins and Gantrez by HPLC with evaporative light scattering detection, Journal of Pharmaceutical and Biomedical Analysis, 2005, pp. 495-502, vol. 39.
Lalloo et al., Membrane transport of camptothecin: facilitation by human P-glycoprotein (ABCBI) and multidrug resistance protein 2 (ABCC2), BMC Medicine, May 4, 2004, vol. 2, pp. 1-12.
Scripture et al., Modulation of cytochrome P450 activity: implications for cancer therapy, Lancet Oncology, 2005, vol. 6, pp. 780-789.
Kuppens et al., Topoisomerase I inhibitors in the treatment of gastrointestinal cancer: from intravenous to oral administration, Clinical Colorectal Cancer, 2004, vol. 4, pp. 163-180.
Arbós, Pau, et al.; "Nanoparticles with specific bioadhesive properties to circumvent the pre-systemic degradation of fluorinated pyrimidines," Journal of Controlled Release, 2004, pp. 55-65, vol. 96.
Gómez, Sara, et al.; GantrezÓ® AN nanoparticles as an adjuvant for oral immunotherapy with allergens, Vaccine, 2007, pp. 5263-5271, vol. 25.

(Continued)

*Primary Examiner* — James Rogers
(74) *Attorney, Agent, or Firm* — Tristan A. Fuierer; Marianna Fuierer; Moore & Van Allen, PLLC

(57) ABSTRACT

The invention relates to nanoparticles comprising a biodegradable polymer, a cyclodextrin or a derivative thereof, and a biologically active molecule. Said nanoparticles can associate large amounts of biologically active molecules, especially of a hydrophobic nature, and release the biologically active molecule providing sustained and constant plasma levels thereof when they are administered orally or through any other mucosa of the organism.

4 Claims, 6 Drawing Sheets

(56) References Cited

OTHER PUBLICATIONS

Schmidt, Ute, et al.; Modification of Poly(octadecene-alt-maleic anhydride) Films by Reaction with Functional Amines, Journal of Applied Polymer Science, 2003, pp. 1255-1266, vol. 87.

* cited by examiner

NANOPARTICLES COMPRISING A CYCLODEXTRIN AND A BIOLOGICALLY ACTIVE MOLECULE AND USES THEREOF

CROSS-REFERENCE TO RELATED APPLICATIONS

This application is filed under the provisions of 35 U.S.C. §371 and claims the priority of International Patent Application No. PCT/ES2008/000269 filed on 18 Apr. 2008 entitled "Nanoparticles Comprising a Cyclodextrin and a Biologically Active Molecule and Uses Thereof" in the name of Maite agüeros Bazo, et al., which claims priority of Spanish Patent Application No. P200701074 filed on 20 Apr. 2007, both of which are hereby incorporated by reference herein in their entirety.

FIELD OF THE INVENTION

The invention relates to nanoparticles, with bioadhesive characteristics, comprising a biodegradable polymer, a cyclodextrin or a derivative thereof, and a biologically active molecule. The invention also relates to a process for producing them, with compositions containing said nanoparticles and with applications thereof.

BACKGROUND OF THE INVENTION

In the last few years, the use of biodegradable polymeric nanoparticles as carriers for the administration of drugs, especially by an oral route, has been developed. Nanoparticles are generally defined as solid particle type colloidal systems, with a size less than one micrometer, formed by natural or synthetic polymers. Depending on the process followed in their preparation, two types of structures can be obtained: nanospheres or nanocapsules. Nanospheres have a polymeric matrix type structure, in which the active ingredient is dispersed, whereas nanocapsules have a core containing the active ingredient, surrounded by a shell, such as a polymeric shell. Due to the high specific surface of these systems the active ingredient can also be adsorbed on the surface of the nanoparticular system.

The oral route is the most popular and attractive route for the administration of medicinal products. The use of this route is associated to a significant increase of the acceptance of the medication by the patient and with lower sanitary costs. However, an important number of drugs have a very low efficacy when they are administered by means of this route. This phenomenon can be due to one or several of the following factors which condition the oral bioavailability of a drug: (i) low permeability of the active molecule for traversing the mucosa (generally associated to hydrophilic drugs), (ii) low stability in the gastrointestinal environment (presence of extreme pH values, enzymes, etc.), (iii) incomplete release of the drug from the dosage form, (iv) low solubility of the active ingredient in the gastrointestinal environment (associated to hydrophobic drugs), and (v) presystemic metabolism.

On a number of occasions, nanoparticulate systems allow, significantly increasing the bioavailability of the biologically active molecule and, therefore, offering new administration strategies. The improvement of the bioavailability obtained after using these carriers can be explained by means of the ability of the polymeric nanoparticles for developing bioadhesive interactions with the gastrointestinal mucosa tract. Thus, when a nanoparticle suspension is administered orally, these carriers can interact and develop adhesive interactions with several components of the mucosa. Depending on certain physicochemical parameters (such as the nature of the polymer, size, surface charge or the presence of certain coatings or ligands in the carrier), the bioadhesive characteristics of the nanoparticles can vary and allow, in certain cases, reaching the enterocyte surface, and, possibly, developing bioadhesive interactions in very specific regions of the gastrointestinal tract. All these phenomena lead to (i) an increase of the residence time of the dosage form in close contact with the surface of the mucosa, or to (ii) a specific location of the carrier (with the drug substance) in a certain area. Once the nanoparticles are adhered to the mucosa, they can promote the absorption of the carried drug and its access to the systemic circulation by means of several mechanisms.

Illustrative examples of drugs the oral bioavailability of which increases by means of their encapsulation or association to nanoparticles include salmon calcitonin, furosemide, avarol, dicumarol, nifedipine, fluoropyrimidines, plasmids, etc.

Homo- and copolymers of lactic and glycolic acids (PLGA) are especially important as biodegradable polymers for manufacturing particulate systems since they have good tissue compatibility, are not toxic and have been used for many years as reabsorbable suture material. These (co) polymers are soluble in organic solvents, such as chloroform, dichloromethane, acetone and ethyl acetate and insoluble in aqueous media; however, they can capture water and swell to a greater or lesser extent, depending on their molecular weight and on their composition. Among the drawbacks of these polymers, it should be emphasized that PLGA can be rather hydrophobic compared to many of the antigens that it carries. Furthermore, both PLGA hydration and degradation are essential requirements for releasing the antigen during the erosion phase. This erosion causes a rather acidic microenvironment due to the accumulation of the polymer degradation products, lactic and glycolic acids; the pH can drop until the order of 2-3. In these conditions, the released proteins undergo hydrolysis and aggregation in the acidified medium and many antigens lose their antigenic capacity. Finally, their high cost could limit their use and would favor the search for other less expensive materials.

As an alternative to polyesters, nanoparticles prepared with other polymers have proven to be suitable for the oral administration of drugs. One of the most used polymers is chitosan. Chitosan is a polymer similar to cellulose coming from the deacetylation of the chitin, the main component of the exoskeleton of crustaceans. Chitosan can be formulated in nanoparticles of different sizes in which it has the drug incorporated. Chitosan particles can increase protein absorption in the mucosal surface, inducing a transient opening of the tight junctions. Furthermore, chitosan can have an immunomodulatory effect, stimulating in vitro cytokine production and improving the natural Th2/Th3 balance at the mucosa level in the absence of antigen.

The methyl vinyl ether and maleic anhydride copolymer (PVM/MA) [Gantrez®] has recently been proposed as a biodegradable material for producing nanoparticles (Arbos et al., J. Control. Release, 83 (2002) 321-330). These PVM/MA copolymers are widely used as thickeners, stabilizers of aqueous solutions, dental adhesive components, transdermal patches and in oral tablets. Among the main advantages of these polyanhydrides, their low cost, their low oral toxicity and the availability of functional groups that can easily react with molecules containing hydroxyl or amino groups should be emphasized (Arbos et al., J. Control. Release, 89 (2003) 19-30). Thus, in an aqueous medium, the anhydride group is hydrolyzed originating two carboxyl groups and this reaction allows easily binding ligands to the polymeric chain or to the surface of the prepared nanoparticles.

Cyclodextrins (CDs) are a group of cyclic oligosaccharides obtained by enzymatic starch degradation of. They are formed by α-1,4-glucopyranose units bound to one another, forming a frustoconical type structure with a hydrophobic internal cavity. CDs can contain more than 15 α-1,4-glucopyranose units, although the most abundant ones contain 6 (α-CD), 7 (β-CD) or 8 (γ-CD) α-1,4-glucopyranose units. In pharmaceutical applications, β-CD and its derivatives are the most used, particularly 2-hydroxypropyl-β-cyclodextrin (OH-β-CD). This CD has a high aqueous solubility, lower toxicity as well as a more hydrophobic cavity compared to the original compound (β-CD). The complexes formed by means of using cyclodextrins can provide the host molecule with stability and increased aqueous solubility, which can lead to increases of the bioavailability of this molecule (e.g. drug) and/or the reduction of side effects. Furthermore, the capacity to increase the loading capacity of liposomes and microparticles has been described in the literature. CDs can also modify the release profile of the encapsulated drug.

A number of antitumor agents are administered parenterally, which causes several problems. Among the main advantages involved in the oral administration of antitumor agents, the increase in the quality of life of the patients as well as the reduction of sanitary costs should be emphasized. This route of administration would allow a continuous exposure of cancer cells to the antitumor drug at a suitable and sustained concentration level, which can improve the therapeutic index and reduce side effects. However, most of these drugs (e.g. paclitaxel) have low bioavailability when administered orally.

Paclitaxel (Taxol®, Bristol Myers Squibb Company), a product extracted from the *Taxus brevifolia* tree, was described for the first time in 1971 and since 1993 it is the most used chemotherapeutic agent against cancer in the whole world. Paclitaxel acts at a cellular level promoting the polymerization of tubulin. The microtubules formed in the presence of paclitaxel are thus extraordinarily stable and non-functional, thus causing cell death by the dynamic and functional incapacity of microtubules for cell division. In Europe, this drug is indicated both as an individual agent and in combination with other oncological treatments for the treatment of ovarian cancer, breast cancer and non-small cell lung cancer, both advanced and metastatic.

The main drawback of this drug lies in its poor oral bioavailability due to its low aqueous solubility and mainly to the first-pass metabolism effect. After oral administration, paclitaxel is substrate of P-glycoprotein, as well as of other members of the ABC (ATP-binding cassette) superfamily, such as BCRP and MRP2. The protein transporter ABC superfamily plays a central role in the defense of the organism against toxic compounds and against some anti-cancer agents. Said proteins (P-glycoprotein, MRP2 and BCRP) are located in the apical area of the intestinal, hepatic and renal membranes, mediating the pumping of xenobiotics and toxins to the intestinal, biliary lumen and urine. Furthermore, both P-glycoprotein and MRP2 are located jointly together with CYP3A4, glutathione S-transferases and UDP-glucuronosyltransferases, which involves a synergistic action in regulating the oral bioavailability of the administered drugs.

Due to the foregoing, paclitaxel is currently formulated for its use in clinical practice and by an intravenous route in a carrier formed by Cremophor EL:ethanol (1:1). For the purpose of preventing and minimizing the toxic effects of Cremophor EL by an intravenous route and improving the therapeutic index of the drug, a new formulation based on encapsulating the drug in albumin nanoparticles called Abraxane® (Green et al. Annals of Oncology 17:1263-1268, 2006) has recently been marketed.

It is therefore necessary to develop drug administration systems which can increase, when administered orally, the bioavailability of a number of active ingredients, especially of those drugs with a lipophilic nature and/or which are a substrate of P-glycoprotein (e.g. paclitaxel). Advantageously, said administration systems should have bioadhesive properties, should have the capacity to incorporate variable amounts of lipophilic drugs, and, ideally, should be able to prevent the effect of P-glycoprotein on the transported drug. These objectives can be achieved by means of the nanoparticles provided by the present invention.

SUMMARY OF THE INVENTION

Surprisingly enough, it has now been found that the association of the nanoparticles of a biodegradable polymer, such as the methyl vinyl ether and maleic anhydride (PVM/MA) copolymer, with cyclodextrins bound to biologically active molecules, allows obtaining nanoparticles with physicochemical characteristics and characteristics of bioadhesion to the gastrointestinal mucosa which make them very interesting systems as transporters of all types of biologically active molecules, especially hydrophobic (lipophilic) biologically active molecules such as paclitaxel. Said nanoparticles can extend the residence time in the mucosa after their oral administration. Furthermore, said nanoparticles can improve the bioavailability of biologically active molecules which may be a substrate of P-glycoprotein. Likewise, said nanoparticles can be used as systems for the administration of drugs with high toxicity (e.g. cytostatics) as they offer sustained and constant plasma levels of the biologically active molecule for time periods of up to 24 hours, which enables possible alternative treatments to hospital perfusion, allowing a reduction of the sanitary cost of treatments with these types of drugs.

Therefore, the invention provides nanoparticles with the capacity to associate large amounts of biologically active molecules, especially of a hydrophobic nature, for their effective administration through mucosas, especially by an oral route, due to the fact that they have suitable bioadhesive characteristics favoring the interaction of the nanoparticles (containing the biologically active molecule) with the surface of the mucosa, they can transport a wide range of biologically active molecules, especially of a lipophilic nature and, above all, they can release the biologically active molecule, providing sustained and constant plasma levels thereof when they are administered orally or through any other mucosa of the organism. If the transported biologically active molecule is a substrate of P-glycoprotein, the nanoparticles of the invention can prevent the action of this protein on the biologically active molecule in question.

The nanoparticles provided by this invention comprise a biodegradable polymer, a cyclodextrin or a derivative thereof, and a biologically active molecule. In particular, it has been found that nanoparticles formed by a polyvinyl methyl ether and maleic anhydride copolymer and β-cyclodextrin (β-CD), 2-hydroxypropyl-β-cyclodextrin (OH-β-CD) or 6-monodeoxy-6-monoamino-β-cyclodextrin (NH-β-CD) are easy to produce and provide excellent characteristics of bioadhesion, size and zeta potential which make them suitable for the administration of hydrophobic biologically active molecules (e.g. paclitaxel). Furthermore, it has been found that the selection of the type of cyclodextrin used in their production allows suitably modulating the characteristics of these nanoparticles which can be advantageously used according to the type of biologically active molecule to be transported and/or the method of administration of the pharmaceutical formulation. Finally, it has been found that the incorporation of paclitaxel in these nanoparticles allows increasing in a very important manner the oral bioavailability thereof, minimizing the effect of P-glycoprotein at the gastrointestinal mucosa level.

Therefore, in a first aspect, the invention relates to nanoparticles comprising a biodegradable polymer, a cyclodextrin or a derivative thereof, and a biologically active molecule, useful for transporting biologically active molecules. In a particular embodiment, the biodegradable polymer is a methyl vinyl ether and maleic anhydride (PVM/MA) copolymer. In another particular embodiment, the cyclodextrin is β-CD, OH-β-CD or NH-βCD.

In a particular embodiment, the biologically active molecule present in the nanoparticles of the invention is paclitaxel. In this case, the nanoparticles allow spectacular increases of the oral bioavailability of paclitaxel, the oral absorption of which is virtually nil due to its physicochemical characteristics (high lipophilicity) and to the fact that it is a substrate of the P-glycoprotein located in the gastrointestinal tract.

In another aspect, the invention relates to a pharmaceutical composition comprising said nanoparticles.

In another aspect, the invention relates to a process for producing said nanoparticles.

DETAILED DESCRIPTION OF THE INVENTION

Nanoparticles

Figure 1:
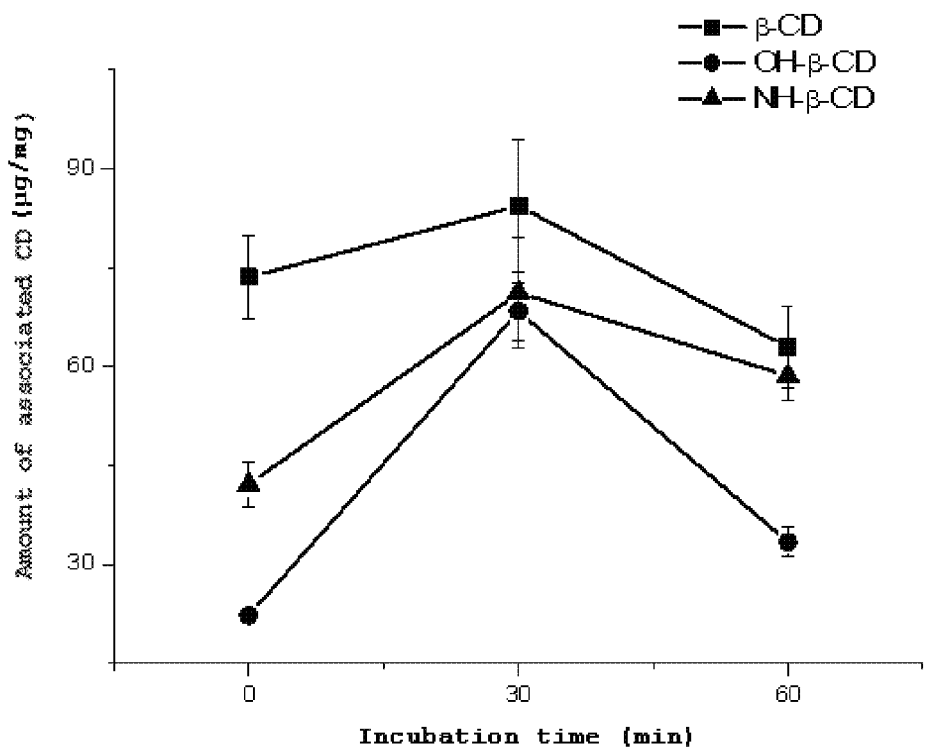
FIG. 1 is a graph showing the variation of the amount of cyclodextrin (CD) associated to the PMV/MA nanoparticles according to the type of CD used [β-CD: β-cyclodextrin; OH-β-CD: 2-hydroxypropyl-β-cyclodextrin; NH-β-CD: 6-monodeoxy-6-monoamino-β-cyclodextrin] and the incubation time of the latter with methyl vinyl ether and maleic anhydride (PVM/MA) copolymer (100 mg) before preparing the nanoparticles. The results show mean±standard deviation (n=8).

In one aspect, the invention relates to nanoparticles, hereinafter nanoparticles of the invention, comprising a biodegradable polymer, a cyclodextrin or a derivative thereof, and a biologically active molecule.

The nanoparticles of the invention have suitable physicochemical characteristics, characteristics of specificity and bioadhesion to the gastrointestinal mucosa, which makes them potentially useful systems for transporting biologically active molecules, particularly lipophilic biologically active molecules (e.g. paclitaxel, etc.) and/or biologically active molecules which are a substrate of P-glycoprotein. The nanoparticles of the invention can improve the bioavailability of biologically active molecules in general, and, in particular, of lipophilic biologically active molecules and/or of biologically active molecules which can be a substrate of P-glycoprotein. In fact, the nanoparticles of the invention can extend the residence time in the mucosa after their oral administration. Likewise, the nanoparticles of the invention can be used as a system for transporting biologically active molecules with high toxicity, for example, cytostatics, due to the fact that they offer sustained and constant plasma levels of such drugs for time periods of up to 24 hours, which allows designing alternative treatments to hospital perfusion, resulting in the reduction of the sanitary cost of the treatments with these types of drugs.

As used herein, the term "nanoparticle" relates to spheres or similar shapes with a mean size less than 1.0 micrometer (μm). The nanoparticles of the invention generally have a mean particle size comprised between 1 and 999 nanometers (nm), preferably between 10 and 900 nm. In a particular embodiment, the nanoparticles of the invention have a mean particle size comprised between 100 and 400 nm.

"Mean size" is understood as the mean diameter of the nanoparticle population moving jointly in an aqueous medium. The mean size of these systems can be measured by standard procedures known by persons skilled in the art and which are described, by way of illustration, in the experimental part accompanying the examples described below. The mean particle size can be influenced mainly by the amount and molecular weight of the biodegradable polymer, by the nature and amount of the cyclodextrin, or derivative thereof, and by the nature and amount of the biologically active molecule, present in the nanoparticles of the invention (generally, the higher the amount or molecular weight of said components, the greater the mean size of the nanoparticle), and by some parameters of the process for producing said nanoparticles, such as the stirring speed, etc.

Biodegradable Polymer

The nanoparticles of the invention comprise a biodegradable polymer. As used herein, the term "biodegradable" relates to polymers that dissolve or degrade in a time period which is acceptable for the desired application, in this case in vivo therapy, once they are exposed to a physiological solution with a pH comprised between 1 and 9, typically between 4 and 9, at a temperature comprised between 25° C. and 40° C.

Virtually any biodegradable polymer known in the state of the art giving rise to the formation of nanoparticles can be used to put the present invention into practice. Illustrative, non-limiting examples of said biodegradable polymers include polyhydroxy acids, such as polylactic acid, polyglycolic acid, etc., and copolymers thereof, e.g. poly(lactic-co-glycolic acid) [PLGA], etc.; polyanhydrides; polyesters; polysaccharides, e.g. chitosan, etc. The molecular weight of said biodegradable polymer can vary within a wide range provided that it complies with the established conditions of forming nanoparticles and being biodegradable.

In a particular embodiment, the biodegradable polymer used is the methyl vinyl ether and maleic anhydride copolymer in anhydride form (PVM/MA). In a specific embodiment, the PVM/MA copolymer marketed under the trade name Gantrez® AN can be used, for example. In a particular embodiment, said PVM/MA copolymer has a molecular weight comprised between 100 and 2,400 kDa, preferably between 200 and 2,000 kDa, more preferably between 180 and 250 kDa. This biodegradable polymer (PVM/MA) is particularly advantageous since it is widely used in pharmaceutical technology due to its low toxicity ($LD_{50}$=8-9 g/kg by an oral route) and excellent biocompatibility. Furthermore, it is easy to obtain, both due to the amount and due to its cost. This biodegradable polymer (PVM/MA) can react with different hydrophilic substances, due to the presence of its anhydride groups, without having to resort to usual organic reagents (glutaraldehyde, carbodiimide derivatives, etc.) which have considerable toxicity. In an aqueous medium, the PVM/MA copolymer is insoluble, but its anhydride groups are hydrolyzed, giving rise to carboxylic groups. The dissolution is slow and depends on the conditions in which it occurs. Due to the availability of functional groups in PVM/MA, the covalent bond of molecules with nucleophilic groups, such as hydroxide or amino, occurs by simple incubation in an aqueous medium.

International patent application WO 02/069938, the content of which is incorporated in this description by reference, describes PVM/MA copolymer nanoparticles. By way of illustration, said PVM/MA copolymer nanoparticles can be easily obtained by the desolvation of the copolymer by means of adding, to an organic solution thereof, a first polar solvent (miscible with a solution of the copolymer) and subsequently adding a second non-solvent liquid, such as a hydroalcoholic solution. Optionally, a cross-linking agent can be added.

Cyclodextrin and its Derivatives

The nanoparticles of the invention comprise, in addition to the biodegradable polymer, a cyclodextrin or a derivative thereof.

As used in this description, the term "cyclodextrin" includes any cyclic oligosaccharide formed by glucose units bound by α-1,4 (α-1,4-glucopyranose) glycosidic bonds. These units occur as a result of an intramolecular transglycosylation reaction of starch degradation by the cyclodextrin glucanotransferase (CGTase) enzyme.

The "cyclodextrin" can contain more than 15 α-1,4-glucopyranose units, although the most abundant ones contain 6, 7 or 8 α-1,4-glucopyranose units, forming the so-called alpha-cyclodextrins (α-CD), beta-cyclodextrins (β-CD) or gamma-cyclodextrins (γ-CD), respectively. All of them have a frustoconical type structure, with a hydrophobic internal cavity and a hydrophilic external face. This is due to the fact that the hydroxyl groups are oriented towards the outside of the cyclodextrin whereas in its hydrophobic internal cavity, it is covered by methylene group hydrogens as well as by ether type oxygens. It can thus act as a host by completely or partially trapping the guest molecule. In a particular embodiment, said cyclodextrin is an alpha-cyclodextrin, a beta-cyclodextrin or a gamma-cyclodextrin.

As used in this description, the term "cyclodextrin derivative" includes any cyclodextrin having at least one modified terminal hydroxyl group. The chemical modification of cyclodextrins can alter their physicochemical properties, improving solubility, stability and controlling the chemical activity of the molecules with which they are bound (guest molecules). The incorporation of alkyl, aryl, carboxyalkyl, cyanoalkyl, hydroxyalkyl, sulfoalkyl, amino, azido, heterocyclic, acetyl, benzoyl, succinyl groups, and other groups containing phosphorus, sulfur, etc. by means of the reaction of the OH groups of cyclodextrins has been described (Robyt (1998) "Essentials of carbohydrate chemistry", Ed. Charles R. Canto, Springer Advanced Text in Chemistry). In a particular embodiment, at least one of said terminal hydroxyl groups is modified, substituting the hydrogen with a linear or branched $C_1$-$C_8$ alkyl group, e.g. methyl, ethyl, propyl, etc.; tri($C_1$-$C_8$)alkylsilyl, e.g. t-butyldimethylsilyl, etc.; $C_1$-$C_8$ hydroxyalkyl, e.g. 2-hydroxyethyl, 2-hydroxypropyl, etc.; ($C_1$-$C_8$)alkylcarbonyl, optionally substituted with a carboxyl group, e.g. acetyl, succinyl, etc.; arylcarbonyl, e.g. benzoyl, etc.; ($C_1$-$C_2$)cyanoalkyl, e.g. cyanomethyl, cyanoethyl; amino, optionally substituted; azido; sulfo; ($C_1$-$C_4$) sulfoalkyl; or with a saccharide radical, e.g. glucosyl, mannosyl, etc. In another particular embodiment, two or more of the terminal hydroxyl groups of a CD, for example, 2, 3, 4, 5, 6, or 7 terminal hydroxyl groups present in a β-CD, are modified by any of said groups.

Parent cyclodextrins (i.e. without derivatization), particularly β-CD, have a limited aqueous solubility compared to acyclic saccharides, partly due to the strong bonds between the molecules of the cyclodextrin in crystalline state. Furthermore, β-CD can form intramolecular hydrogen bonds between the secondary hydroxyl groups, thus producing unfavorable enthalpies of solution, and, therefore, a low aqueous solubility. The substitution of any of the hydrogen bonds with hydrophobic groups, such as methoxy- or ethoxy-, results in the increase of aqueous solubility. For example, the aqueous solubility of β-CD is 1.85% (w/v) at room temperature, but it could increase up to 150 times upon increasing the degree of methylation (methyl-β-CD). Another particularly important cyclodextrin derivative is 2-hydroxypropyl-β-cyclodextrin (OH-β-CD), obtained after the treatment of β-CD with propylene oxide, which has an aqueous solubility of 60% (w/v). Likewise, these derivatives can improve the toxicological profile, the capacity to encapsulate biologically active molecules and modulate their release profile. The main problem of parent cyclodextrins is the nephrotoxicity after being administered parenterally, mainly for β-CD, due to its low aqueous solubility. Therefore, the most hydrophilic derivatives, such as OH-β-CD, reduce these nephrotoxicity problems as they can be more easily eliminated. The same does not occur for methylated β-CD derivatives, which, despite being more soluble than β-CD, would not be exempt from causing systemic toxicity due to their greater capacity to interact with endogenous lipids, which limits their parenteral use. On the contrary, toxicity studies carried out after oral administration show that cyclodextrins as well as their derivatives are not toxic by this route.

Cyclodextrins are water-soluble macromolecules which have been approved for oral, parenteral and topical administration of drugs. The applications of cyclodextrins in the oral administration of drugs are mainly due to the improvement in the oral bioavailability of the drug, due to the increase of the solubility, the increase of the stability of the drug in the gastrointestinal tract and/or in the formulation. Furthermore, for certain drugs, the potential of cyclodextrins in reducing the local irritation caused by the drug itself, the control of the release of the drug throughout the gastrointestinal tract or the masking of unwanted organoleptic characteristics, among others, is interesting. Such is the case of the itraconazole, which is marketed in United States and Europe associated to OH-β-CD for its oral administration, significantly reducing the irritation caused in the gastrointestinal tract when administered in an isolated manner.

In addition, cyclodextrins are also used due to their capacity to increase the permeability of the drug through skin and mucosas, which causes a better and more uniform absorption of the drug. This leads to an increase of the activity of the drug after its administration, such as, for example, the complex formed between flutamide and OH-β-CD, substantially improving the absorption of the drug after its oral administration.

In a particular embodiment, said cyclodextrin derivative is an alpha-cyclodextrin derivative, or a beta-cyclodextrin derivative, or a gamma-cyclodextrin derivative. Illustrative, non-limiting examples of cyclodextrin derivatives that can be used to put the present invention into practice include ethyl-β-CD, heptakis(2,3,6-tri-O-ethyl)-β-CD, 2-hydroxypropyl-β-CD, 2-O-2-hydroxypropyl-β-CD, 2-hydroxyethyl-β-CD, succinylated β-CD derivatives, succinylated 2-hydroxypropyl-β-CD derivatives, butyl-β-CD, heptakis(2,6-di-O-n-butyl)-β-CD, heptakis(2,6-di-O-n-pentyl)-β-CD, methyl-β-CD, methyl-β-CD, carboxymethyl-β-CD, carboxyethyl-β-CD, heptakis(2,6-di-O-methyl)-β-CD, heptakis(2,3,6-tri-O-methyl)-β-CD, acetyl-β-CD, heptakis(3-O-acetyl-2,6-di-O-n-pentyl)-β-CD, heptakis(3-O-acetyl-2,6-di-O-methyl)-β-CD, sulfo-β-CD, sulfapropyl-β-CD, n-butyl-β-CD, heptakis(3-O-n-butyryl-2,6-di-O-pentyl)-β-CD, 2-cyanoethyl-β-CD, 6-monodeoxy-6-monoazido-β-CD, heptakis(2,3,6-tri-O-benzyl)-β-CD, heptakis(2,3,6-tri-O-benzoyl)-β-CD, 6-monodeoxy-6-monoamino-β-CD, heptakis(2,6-di-O-n-pentyl-3-O-trifluoroacetyl)-β-CD, heptakis(2,3,6-tri-O-n-octyl)-β-CD, heptakis(2,3-di-O-acetyl-6-O-tert-butyldimethylsilyl)-β-CD, heptakis(6-O-tert-butyldimethylsilyl)-β-CD, heptakis (6-O-tert-butyldimethylsilyl-2,3-di-O-methyl)-β-CD, heptakis(2,6-di-tert-butyldimethylsilyl)-β-CD, heptakis(2,3,6-tri-O-trifluoroacetyl)-β-CD, heptakis(2,6-di-O-methyl-3-O-n-pentyl)-β-CD.

The weight ratio between the cyclodextrin, or derivative thereof, and the biodegradable polymer can vary within a wide range, in a particular embodiment, said cyclodextrin (or derivative thereof): biodegradable polymer weight ratio is 1:1-10, preferably 1:1-5, more preferably about 1:4. In a particular embodiment, said biodegradable polymer is PVM/MA.

As has been previously mentioned, in pharmaceutical applications, β-CD and its derivatives are the most used, particularly 2-hydroxypropyl-β-cyclodextrin (OH-β-CD) since it has high aqueous solubility, low toxicity and a more hydrophobic cavity than that of β-CD.

In a particular embodiment, the cyclodextrin present in the nanoparticles of the invention does not have any substituted hydroxyl group. In a specific embodiment, said cyclodextrin is beta-cyclodextrin (β-CD), containing 7 α-1, 4-glucopyranose units. Although the β-CD:biodegradable polymer weight ratio is 1:1-10, preferably 1:1-5, 1:4 ratios give good results. By way of illustration, approximately 0.25 mg of β-CD/mg of biodegradable polymer gives an efficient association. In this case, the amount of β-CD associated to the nanoparticles is approximately 90 micrograms/mg of nanoparticle. These nanoparticles are characterized by generally having a spherical shape and a size close to 150 nm.

In another particular embodiment, the cyclodextrin present in the nanoparticles of the invention is a more hydrophilic β-CD derivative, such as a hydroxylated β-CD derivative comprising one or more hydroxyalkyl groups (e.g. hydroxypropyl). In a preferred particular embodiment, 2-hydroxypropyl-β-cyclodextrin (OH-β-CD) is used. The OH-β-CD:biodegradable polymer weight ratio is 1:1-10, preferably 1:1-5, although a 1:4 weight ratio gives good results. By way of illustration, approximately 0.25 mg of OH-β-CD/mg of biodegradable polymer gives an efficient association. In this case, the amount of β-CD associated to the nanoparticles is approximately 65 micrograms/mg of nanoparticle. These nanoparticles are characterized by generally having a spherical shape and a size close to 150 nm.

In another particular embodiment, the cyclodextrin present in the nanoparticles of the invention is a derivative of a CD having one or more terminal functional groups different from hydroxyl, e.g. one or more optionally substituted amino groups. The amino groups can in turn be substituted and have other functional groups, e.g. $C_1$-$C_4$ alkyl; illustrative examples of said substituted amino groups include methylamine, ethylamine, diethylamine, etc.). In a preferred particular embodiment, said amino group is a free amino group, without substitution (—$NH_2$). In several performed assays, it has been observed that with said groups, the nanoparticles of the invention administered orally are accumulated on certain intestinal tract segments, which allows a specific administration. In a specific embodiment, the cyclodextrin derivative present in the nanoparticles of the invention is 6-monodeoxy-6-monoamino-β-cyclodextrin (NH-β-CD). The NH-β-CD:biodegradable polymer weight ratio is 1:1-10, preferably 1:1-5, although a 1:4 ratio gives good results. These nanoparticles are characterized by generally having a spherical shape and a size close to 150 nm.

In a particular embodiment, the cyclodextrin, or derivative thereof, present in the nanoparticles of the invention is selected from the group consisting of β-cyclodextrin (β-CD), 2-hydroxypropyl-β-cyclodextrin (OH-β-CD), 6-monodeoxy-6-monoamino-β-cyclodextrin (NH-β-CD) and mixtures thereof.

Several assays performed by the inventors have shown that the nanoparticles based on a biodegradable polymer containing cyclodextrin allow the formation of direct bioadhesive interactions between these carriers (nanoparticles) and components of the surface of the gastrointestinal tract. This close contact is interesting for increasing the bioavailability of biologically active molecules when they are administered through any route giving access to a mucosa (e.g. oral, rectal, vaginal, ocular or nasal route).

The nanoparticles based on a biodegradable polymer (e.g. PVM/MA) containing cyclodextrin (empty nanoparticles, i.e. without a biologically active molecule) can be obtained by a process based on the solvent displacement method described, for example, in international patent application WO 02/069938. By way of illustration, said empty nanoparticles comprising a biodegradable polymer (e.g. PVM/MA) and a cyclodextrin, or a derivative thereof, can be obtained by two alternative processes, specifically, by means of simultaneously incubating the two components, the biodegradable polymer (e.g. PVM/MA) and cyclodextrin or derivative thereof (e.g. β-CD, OH-β-CD or NH-β-CD) in the organic phase [alternative 1], or by means of incubating the biodegradable polymer (e.g. PVM/MA) nanoparticles with an aqueous solution of cyclodextrin, or a derivative thereof (e.g. β-CD, OH-β-CD or NH-β-CD) [alternative 2].

Biologically Active Molecule

The nanoparticles of the invention comprise, in addition to the biodegradable polymer and a cyclodextrin or a derivative thereof, a biologically active molecule.

As used herein, the term "biologically active molecule", relates to any substance which is administered to a subject, preferably a human being, with prophylactic or therapeutic purposes; i.e. any substance that can be used in the treatment, cure, prevention or diagnosis of a disease or for improving the physical and mental well-being of humans and animals. Said "biologically active molecule" term generally includes both drugs and antigens and allergens.

The nanoparticles of the invention can incorporate one or more biologically active molecules independently of the solubility characteristics thereof, although said nanoparticles have proven to be a particularly useful system for administering hydrophobic biologically active molecules.

The nanoparticles of the invention allow modifying the distribution of the biologically active molecule distribution that they contain when they are administered by any route giving access to any mucosa of the organism (e.g. oral, rectal, nasal, vaginal, ocular route, etc.).

The chemical nature of the biologically active molecule can vary within a wide range, from small molecules to macromolecular compounds (peptides, polynucleotides, etc.).

In a particular embodiment, said biologically active molecule is a peptide or a protein. As used herein, the term "peptide" relates to a compound formed by amino acids bound by means of peptide bonds and includes oligopeptides (formed by 10 or less amino acids) and polypeptides (formed by more than 10 amino acids). Likewise, as used herein, the term "protein", relates to macromolecules with a high molecular mass formed by linear chains of amino acids bound by means of peptide bonds; the proteins can be formed by one or several peptide chains.

In another particular embodiment, said biologically active molecule is a nucleoside, a nucleotide, an oligonucleotide, a polynucleotide or a nucleic acid. As used herein, an "oligonucleotide" is a polymer of nucleotides bound by 5'-3' phosphodiester bonds with a length equal to or less than 50 nucleotides, whereas a "polynucleotide" is a polymer of nucleotides bound by 5'-3' phosphodiester bonds with a length greater than 50 units. Likewise, the term "nucleic acid" also relates to a polymer of nucleotides bound by 5'-3' phosphodiester bonds; depending on if they are ribonucleotides or deoxyribonucleotides the nucleic acid will be RNA or DNA, respectively. The nucleic acids have different functions in the cells of the live organisms such as the storage of genetic information and its transfer to the next generation (DNA) or the expression of this information during protein synthesis (mRNA and tRNA), they are a structural component of cell organelles, such as ribosomes (rRNA), they catalyze certain chemical reactions (ribozymes) and participate in gene expression regulation mechanisms (by means of complementary RNAs of mRNA or dsRNA in RNA interference).

In another particular embodiment, said biologically active molecule is a small (organic or inorganic) molecule; generally, these molecules are obtained by chemical synthesis or semisynthetic methods or, alternatively, they are isolated from their sources. In a specific embodiment, said small (organic or inorganic) molecule, has a relatively low molecular weight, generally equal to or less than 5,000, typically, equal to or less than 2,500, advantageously, equal to or less than 1,500. A number of therapeutic active ingredients contain these characteristics and can therefore be used to put the present invention into practice.

Although the biologically active molecule present in the nanoparticles of the invention can be both a hydrophilic substance and a hydrophobic substance, in a particular embodiment, the nanoparticles of the invention are particularly useful for administering hydrophobic biologically active molecules. Therefore, in a particular embodiment, the biologically active molecule present in the nanoparticles of the invention is a hydrophobic substance. As used herein, a "hydrophobic substance" is a substance which, due to its properties or composition, is not very soluble in aqueous media, typically having a solubility less than 1% (1 gram of active ingredient per 100 ml of aqueous solvent) at 20° C., at a pH comprised between 1-7.5 and atmospheric pressure.

Virtually any hydrophobic biologically active molecule can be used to put the present invention into practice. Illustrative, non-limiting, examples of hydrophobic biologically active molecules which can be present in the nanoparticles of the invention include antiparasitic agents (e.g. albendazole, mebendazole, praziquantel, etc.); antifungal agents (e.g. clotrimazole, itraconazole, etc.), antibiotics (e.g. sulfamethizole, gentamicin, griseofulvin, etc.), cardiotonic agents (e.g. digoxin, etc.), antitumor agents (e.g. camptothecin, methotrexate, docetaxel, fluorouracil, paclitaxel, etc.), immunosuppressive agents (e.g. tacrolimus, cyclosporine), (gluco)corticoids (e.g. cortisone, dexamethasone, prednisolone, prednisone, triamcinolone, etc.), etc.

In another particular embodiment, the biologically active molecule present in the nanoparticles of the invention is a substance that is a substrate of P-glycoprotein. In fact, an important application of the nanoparticles of the invention lies in their capacity to minimize the negative effect of P-glycoprotein on the absorption through mucosas of a certain drug.

As is known, P-glycoprotein (PGY1; enzyme EC 3.6.3.44) is a protein which, in human beings, is encoded by the ABCB1 gene, also called MDR1 (multidrug resistance 1) gene. P-glycoprotein acts as a transmembrane transporter or pump which transfers its substrates (generally drugs and other xenobiotics) from its intracellular domain to its extracellular domain. Depending on its anatomical location, P-glycoprotein performs its function in 3 main ways: (1) P-glycoprotein limits the entry of the drug substance in the organism after its oral administration as a result of its expression in the enterocyte luminal membrane; (2) once the drug has reached the blood circulation, the P-glycoprotein promotes its elimination in bile and in urine, as a result of its expression in the canalicular membrane of hepatocytes and in the luminal membrane of kidney proximal tubule cells; and (3) once in the systemic blood circulation, it limits the penetration of the drug in sensitive tissues.

Therefore, a substrate substance of P-glycoprotein relates to a substance, e.g. a xenobiotic, with the affinity to bind to the intracellular domain of P-glycoprotein such that, by means of ATP consumption, it can be transported outside the cell according to the following reaction:

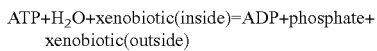

ATP+H$_2$O+xenobiotic(inside)=ADP+phosphate+ xenobiotic(outside)

Illustrative, non-limiting examples of known substrates of P-glycoprotein which can be present in the nanoparticles of the invention as biologically active molecules include, among others (Fromm M F; Trends 2004; 25: 423-429), antitumor agents (e.g. docetaxel, etoposide, imatinib, paclitaxel, teniposide, vinblastine, vincristine, anthracyclines (e.g. doxorubicin, daunorubicin, epirubicin, etc.), etc.); β-adrenoceptor antagonists (e.g. bunitrolol, carvedilol, celiprolol, talinolol, etc.); Ca$^{2+}$ channel blockers (e.g. diltiazem, mibefradil, verapamil, etc.); cardiotonic drugs (e.g. digitoxin, digoxin, quinidine, etc.), antiviral agents (e.g. amprenavir, indinavir, nelfinavir, saquinavir, ritonavir, etc.); steroids (e.g. dexamethasone, methylprednisolone, etc.); immunosuppressive agents (e.g. cyclosporine A, sirolimus, tacrolimus, etc.); antiemetic drugs (domperidone, ondansetron, etc.); antibiotics (e.g. erythromycin, levofloxacin, etc.); antilipidemic agents (e.g. atorvastatin, lovastatin, etc.); histamine H$_1$ receptor antagonists (e.g. fexofenadine, terfenadine, etc.); and drugs of other therapeutic groups (e.g. amitriptyline, colchicine, debrisoquine, itraconazole, losartan, morphine, phenyloin, rifampin, actinomycin D, topotecan, estradiol, rapamycin, FK506, etc).

In a particular embodiment, said biologically active molecule is a hydrophobic substance or a substrate substance of the P-glycoprotein enzyme selected from the group consisting of actinomycin D, albendazole, amitriptyline, amprenavir, atorvastatin, bunitrolol, camptothecin, carvedilol, celiprolol, cyclosporine, clotrimazole, colchicine, cortisone, daunorubicin, debrisoquine, dexamethasone, digitoxin, digoxin, diltiazem, docetaxel, domperidone, doxorubicin, epirubicin, erythromycin, estradiol, etoposide, phenyloin, fexofenadine, FK506, fluorouracil, gentamicin, griseofulvin, imatinib, indinavir, itraconazole, levofloxacin, losartan, lovastatin, mebendazole, methylprednisolone, methotrexate, mibefradil, morphine, nelfinavir, ondansetron, paclitaxel, praziquantel, prednisolone, prednisone, quinidine, rapamycin, rifampicin, saquinavir, sirolimus, sulfamethizole, ritonavir, tacrolimus, talinolol, teniposide, terfenadine, topotecan, triamcinolone, verapamil, vinblastine, vincristine and mixtures thereof.

In a preferred embodiment, the biologically active molecule present in the nanoparticles of the invention is paclitaxel.

In a particular embodiment, the pharmaceutical composition of the invention comprises nanoparticles of the invention containing one or more different drugs. Illustrative, non-limiting examples of said drugs include agents belonging to different therapeutic groups, for example, antitumor agents, β-adrenoceptor antagonists, analgesic agents, Ca$^{2+}$ channel blockers, cardiotonic drugs, antiviral agents, steroids, immunosuppressive agents, antiemetic drugs, antibiotics (e.g. antibacterial, antifungal, antiviral, antiparasitic agents, etc.) antilipidemic agents, histamine H$_1$ receptor antagonists, anti-inflammatory agents, neuroprotectors, anti-allergic agents, antiasthmatic agents, antibiotics, pulmonary surfactants, etc.

As can be observed, some biologically active molecules which are a substrate of P-glycoprotein, have a hydrophobic nature. Likewise, the system for administering biologically active molecules provided by the present invention contemplates the possibility of administering drugs of a number of therapeutic groups.

In another particular embodiment, the pharmaceutical composition of the invention comprises nanoparticles of the invention containing one or more different antigens for vaccine purposes or one or more different allergens for immunotherapeutic purposes as a biologically active molecule.

As used in this description, the term "antigen" relates to any substance which can be recognized by the immune system of a subject and/or can induce in a subject a humoral immune response or a cellular immune response leading to the activation of B and/or T cells when it is introduced in a subject; by way of illustration, said term includes any native or recombinant immunogenic product obtained from a higher organism or from a microorganism, for example a bacterium, a virus, a parasite, a protozoan, a fungus, etc., which contains one or more antigenic determinants, for example, structural components of said organisms; toxins, for example, exotoxins, etc. Virtually any antigen can be used in the preparation of nanoparticles of the invention loaded with antigen. By way of a non-limiting illustration, the term "antigen" includes:

"microbial" antigens, i.e. antigens of microorganisms, including but without being limited to infectious viruses, bacteria, fungi and parasites; said antigens include the intact microorganism as well as parts, fragments and derivatives thereof, of natural or artificial origin, as well as synthetic or recombinant products which are identical or similar to the natural antigens of a microorganism and induce a specific immune response for this microorganism; in this sense, a compound is similar to a natural antigen of a microorganism if it induces a (humoral and/or cellular) immune response like that of the natural antigen of this microorganism; said antigens are routinely used by persons skilled in the art; and "tumor" antigens, i.e. substances, for example peptides, associated to a tumor or a cancer ("tumor marker"), which can cause an immune response, particularly when presented in the context of a molecule of the MHC, e.g. Her2 (breast cancer); GD2 (neuroblastoma); EGF-R (malignant glioblastoma); CEA (medullary thyroid cancer); CD52 (leukemia); human melanoma gp100 protein; human melanoma melan-A/MART-1 protein; tyrosinase; NA17-A nt protein; MAGE-3 protein; p53 protein; HPV16E7 protein; antigenic fragments of said antigens; etc.

As used in this description, the term "allergen" relates to a substance to which a subject is sensitive and causes an immune reaction, for example, pollen allergen extracts, insect allergen extracts, food or food product allergen extracts, components present in saliva, pincers or stings of insects inducing a sensitivity reaction in a subject, components present in plants inducing a sensitivity reaction in a subject, etc., for example, pollen protein extracts, such as graminaceous pollen, allergenic *Lolium perenne* extracts, allergenic olea (olive) extracts, etc.; insect protein extract, such as from dust mites, etc.; allergenic food component extracts, etc. Virtually any allergen can be used in the preparation of the nanoparticles loaded with allergen of the composition of the invention; nevertheless, in a particular embodiment, said allergen is ovalbumin (OVA), a protein widely used as an experimental allergenic model.

Illustrative, non-limiting examples of said biologically active molecules which can contain the nanoparticles of the invention include bacterial antigens: cytoplasmic, periplasmic, cell envelope antigens (e.g. inner membrane proteins, outer membrane proteins, lipopolysaccharides and mixed complexes, proteins associated to the cell wall, etc.), etc.; antigens of surface structures (e.g. fimbriae, glycocalix, flagella, etc.), including those of intracellular pathogens, such as for example, *Brucella* sp., *Salmonella* sp., etc; both soluble and surface antigens of eukaryotic microorganisms; viral antigens, for example, matrix, capsid, envelope, internal (including enzymatic) antigens, allergens of animal species (mites, etc.), of plants (gramineae, etc.), etc.

The nanoparticles of the invention can be obtained by means of a process based on the solvent displacement method described, for example, in international patent application WO 02/069938, which comprises (i) forming a (cyclodextrin or derivative thereof)-(biologically active molecule) complex, hereinafter [CD:BAM] complex, and (ii) incorporating said [CD:BAM] complex in a solution of the biodegradable polymer in an organic solvent before the formation of nanoparticles.

Briefly, the formation of said [CD:BAM] complex comprises adding a solution of the biologically active molecule (BAM) in an organic solvent, such as an alcohol, ethanol for example, to an aqueous solution of the cyclodextrin or derivative thereof (CD). The mixture is subjected to stirring until reaching equilibrium. Water and the organic solvent (e.g. ethanol) are then eliminated by any suitable conventional method, for example, under reduced evaporation or any other system for eliminating solvents.

The CD:BAM molar ratio present in said [CD:BAM] complex can vary within a wide range depending on, among other factors, the cyclodextrin or derivative thereof (CD) and on the biologically active molecule (BAM) present in said complex; nevertheless, in a particular embodiment, the CD:BAM molar ratio present in said [CD:BAM] complex is 1:1-4, typically 1:1-2. In a specific embodiment, when the biologically active molecule is paclitaxel, the CD:BAM molar ratio in said [CD:BAM] complex is 1:1.

The incorporation of said [CD:BAM] complex in a solution of the biodegradable polymer in an organic solvent before the formation of nanoparticles can be carried out by means of adding said complex to the solution of biodegradable polymer and subsequently simultaneously incubating both components, the biodegradable polymer (e.g. PVM/MA) and the [CD:BAM] complex, in the organic phase (e.g. acetone) comprising the biodegradable polymer (e.g. PVM/MA), for a suitable time period, typically comprised between 10 and 60 minutes, at a temperature comprised between 20° C. and 30° C. approximately (in a particular embodiment, when the biologically active molecule is paclitaxel, the incubation can be carried out for a time period of 30 minutes at room temperature (25° C.)), under stirring, for example, by means of using an ultrasound, magnetic or mechanical stirrer); by operating in this way, a high degree of association of the [CD:BAM] complex to the biodegradable polymer is generally obtained. Briefly, this step comprises simultaneously dissolving and/or dispersing the biodegradable polymer and the [CD:BAM] complex in an organic solvent (e.g. acetone). The mixture is incubated under stirring at room temperature for a certain time period. The concentration of the biodegradable polymer is preferably comprised between 0.001% and 10% w/v and that of the [CD:BAM] complex between 0.001% and 5% w/v. Optionally, if desired, a certain volume of a polar solvent miscible with the solution of the polymers (e.g. ethanol) is added on said solution. Also, optionally, if desired, a cross-linking agent can be used to improve the stability of the nanoparticles, as described in WO 02/069938. Illustrative examples of cross-linking agents which can be used include diaminated molecules (e.g. 1,3-diaminopropane, etc.), polysaccharides or simple saccharides, proteins, and generally any molecule having functional groups which can react with the groups present in the biodegradable polymer, for example, with the anhydride groups present in PVM/MA. Nevertheless, it is generally not necessary to cross-link since this occurs simultaneously due to the presence of the cyclodextrin or derivative thereof. In the event that cross-linking was desired, a small amount of any of the indicated products should be added.

Then, in order to form the nanoparticles of the invention, a similar volume of a second non-solvent liquid, preferably a hydroalcoholic solution, is added on the previous mixture. In a particular embodiment, pharmaceutical quality water (purified water or water for injectables (wfi), according to the application) is used. The organic phase:hydroalcoholic solution ratio is preferably included within the range comprised between 1:1 and 1:10 by volume. The nanoparticles are formed instantaneously in the medium, under the appearance of a milky suspension. The organic solvents can be eliminated by any suitable process such as evaporation under reduced pressure, the nanoparticles remaining in a stable aqueous suspension. If desired, the nanoparticles can possibly be purified by conventional means such as centrifugation, ultracentrifugation, tangential filtration, or evaporation, including the use of vacuum. Finally, if desired, the nanoparticles can be lyophilized for their long-term storage and preservation. To facilitate the lyophilization, common cryoprotective agents such as sucrose, lactose or mannitol can be used, preferably at a concentration comprised between 0.1% and 10% by weight.

Alternatively, the nanoparticles of the invention based on a biodegradable polymer can be obtained by means of a process which comprises incubating the biodegradable polymer (e.g. PVM/MA) nanoparticles with an aqueous solution comprising the [CD:BAM] complex. Briefly, this alternative comprises dissolving the biodegradable polymer in an organic solvent, such as acetone. Subsequently, a certain volume of hydroalcoholic solution, such as ethanol, and finally, a similar volume of water are added on this solution. The nanoparticles are formed instantaneously in the medium under the appearance of a milky suspension. The organic solvents are eliminated in a manner similar to that described in the previous process, for example by evaporation under reduced pressure, the nanoparticles remaining in a stable aqueous suspension. The nanoparticles of biodegradable polymer are then incubated in an aqueous solution comprising the previously obtained [CD:BAM] complex. The incubation of the nanoparticles of biodegradable polymer with the [CD:BAM] complex can be carried out under stirring (e.g. by means of using an ultrasound, magnetic or mechanical stirrer) for a certain time period at a suitable temperature in conditions similar to those mentioned in relation to the previous process (e.g. for a time period generally comprised between 10 and 60 minutes, at a temperature comprised between 20° C. and 30° C.). The nanoparticles are subsequently purified by conventional methods, centrifugation for example, and, finally, they are lyophilized, if desired, following the same previously described processes.

The BAM:biodegradable polymer weighted ratio present in the nanoparticles of the invention can vary within a wide range depending on, among other factors, the biodegradable polymer (e.g. PVM/MA) and on the biologically active molecule (BAM) present in said nanoparticles; nevertheless, in a particular embodiment, the BAM:biodegradable polymer weight ratio present in said nanoparticles of the invention is 1:4-20, preferably, 1:10.

The [CD-BAM] complex:biodegradable polymer ratio present in the nanoparticles of the invention can vary within a wide range depending on, among other factors, the biodegradable polymer (e.g. PVM/MA), on the cyclodextrin or derivative thereof and on the biologically active molecule (BAM) present in said nanoparticles; nevertheless, in a particular embodiment, the [CD-BAM] complex:biodegradable polymer weight ratio present in said nanoparticles of the invention is 1:1-20, advantageously 1:2-20, preferably, 3:10 (approximately 1:3.3), by weight.

In a particular embodiment, the biodegradable polymer is PVM/MA.

In another particular embodiment, the biologically active molecule is paclitaxel.

In another particular embodiment, the cyclodextrin derivative is β-cyclodextrin (β-CD), 2-hydroxypropyl-β-cyclodextrin (OH-β-CD) or 6-monodeoxy-6-monoamino-β-cyclodextrin (NH-β-CD).

In another particular embodiment, the biologically active molecule is paclitaxel and the (cyclodextrin or derivative thereof):paclitaxel molar ratio is 1:1.

In a specific embodiment, the [CD:BAM] complex is a β-CD:paclitaxel complex, in a 1:1 molar ratio, and the paclitaxel:biodegradable polymer (e.g. PVM/MA) weight ratio is 1:4-20, although ratios close to 1:10 give good results. By way of illustration, approximately 0.25 mg of paclitaxel in the β-CD:paclitaxel complex, in a 1:1 molar ratio, per mg of polymer gives an efficient association. In this case, the amount of drug associated to the nanoparticles is approximately 40 micrograms of paclitaxel/mg of nanoparticle. These nanoparticles are characterized by having a spherical shape and a size close to 300 nm.

In another specific embodiment, the [CD:BAM] complex is an OH-β-CD complex, in a 1:1 molar ratio, and the paclitaxel:biodegradable polymer (e.g. PVM/MA) weight ratio is 1:4-20, although ratios close to 1:10 give good results. By way of illustration, approximately 0.25 mg of paclitaxel in the OH-β-CD:paclitaxel complex, in a 1:1 molar ratio, per mg of polymer gives an efficient association. In this case, the amount of drug associated to the nanoparticles is approximately 170 micrograms of paclitaxel/mg of nanoparticle. These nanoparticles are characterized by having a spherical shape and a size close to 300 nm.

In another specific embodiment, the [CD:BAM] complex is an NH-β-CD complex, in a 1:1 molar ratio, and the paclitaxel:biodegradable polymer (e.g. PVM/MA) weight ratio is 1:4-20, although ratios close to 1:10 give good results. By way of illustration, approximately 0.25 mg of paclitaxel in the OH-β-CD:paclitaxel complex, in a 1:1 molar ratio, per mg of polymer gives an efficient association. In this case, the amount of drug associated to the nanoparticles is approximately 100 micrograms of paclitaxel/mg of nanoparticle. These nanoparticles are characterized by having a spherical shape and a size close to 300 nm.

In a particular embodiment, when a dose of 10 mg/kg of paclitaxel formulated in nanoparticles of the invention with β-CD is administered orally, constant and sustained plasma levels are obtained for at least 24 hours, after reaching the maximum plasma concentration (Cmax) in a time of approximately 5 hours. The maximum plasma concentration (Cmax) is similar to that obtained after the intravenous administration of the commercial formulation. The area under the plasma curve (AUC) of paclitaxel obtained by this formulation is approximately 5 times greater than that obtained by the intravenous administration of the commercial medicinal product administered at the same dose. This formulation is characterized by offering a mean residence time (MRT) of the drug in the organism approximately 4 times greater than that obtained after the intravenous administration of the commercial formulation.

In another particular embodiment, when a dose of 10 mg/kg of paclitaxel formulated in nanoparticles of the invention with OH-β-CD is administered orally, constant and sustained plasma levels are obtained for at least 24 hours, after reaching the maximum plasma concentration (Cmax) in a time of approximately 6 hours. The maximum plasma concentration is 2 times greater than that obtained after the intravenous administration of the commercial formulation. The area under the plasma curve (AUC) of paclitaxel obtained by this formulation is approximately 5 times greater than that obtained by the intravenous administration of the commercial medicament administered at the same dose. This formulation is characterized by offering a mean residence time (MRT) of the drug in the organism approximately 3.5 times greater than that obtained after the intravenous administration of the commercial formulation.

In another particular embodiment, when a dose of 10 mg/kg of paclitaxel formulated in nanoparticles of the invention with NH-β-CD is administered orally, constant and sustained plasma levels are obtained for at least 24 hours, after reaching the maximum plasma concentration (Cmax) in a time of approximately 4.7 hours. The maximum plasma concentration is approximately half of that obtained after the intravenous administration of the commercial formulation. The area under the plasma curve (AUC) of paclitaxel obtained by this formulation is approximately similar to that obtained by the intravenous administration of the commercial medicinal product administered at the same dose. This formulation is characterized by offering a mean residence time (MRT) of the drug in the organism approximately 3 times greater than that obtained after the intravenous administration of the commercial formulation.

Pharmaceutical Compositions

In another aspect, the invention relates to a pharmaceutical composition comprising at least a nanoparticle of the invention and a pharmaceutically acceptable excipient, carrier or adjuvant.

Said biologically active molecule will generally form a complex with the cyclodextrin or derivative thereof and said complex will mainly be inside the nanoparticle of the invention; nevertheless, it could happen that a relative proportion of said complex containing the biologically active molecule were also bound to the surface of the nanoparticle although most of it is inside (e.g. encapsulated) the nanoparticles of the invention.

The nanoparticles of the invention can be used to modify the distribution of the associated biologically active molecule when they are administered by a route giving access to any mucosa of the organism (including the oral, rectal, nasal, vaginal or ocular route). Additionally, it can also be administered parenterally.

Examples of pharmaceutical compositions include any liquid composition (suspension or dispersion of the nanoparticles) for oral, buccal, sublingual, topical, ocular, nasal, vaginal or parenteral administration; any composition in the form of a gel, ointment, cream or balm for its topical, ocular, nasal or vaginal administration; or any solid composition (tablets, capsules) for its oral administration. In a particular embodiment, the pharmaceutical composition is administered orally. In another particular embodiment, said pharmaceutical composition is administered parenterally.

The described pharmaceutical compositions will comprise the suitable excipients for each formulation. For example, in the case of oral formulations in the form of tablets or capsules, binding agents, disintegrants, lubricants, filler agents, enteric coating, etc. will be included, if necessary. Oral solid formulations are conventionally prepared by mixing, wet or dry granulation and incorporating the nanoparticles of the invention. The pharmaceutical compositions can also be adapted for their parenteral administration in the form of, for example, sterile solutions, suspensions or lyophilized products, in the suitable dosage form; in this case, said pharmaceutical compositions will include the suitable excipients, such as buffers, surfactants, etc. In any case, the excipients will be chosen according to the selected pharmaceutical dosage form. A review of the different pharmaceutical dosage forms of drugs and of their preparation can be found in the book "Tratado de Farmacia Galénica", by C. Faulí i Trillo, 10$^{th}$ Edition, 1993, Luzán 5, S. A. de Ediciones.

The proportion of the biologically active molecule incorporated in the nanoparticle of the invention can vary within a wide range, for example, it can be up to 25% by weight in relation to the total weight of the nanoparticles. Nevertheless, the suitable proportion will depend in each case on the incorporated biologically active molecule.

The dose of nanoparticles of the invention to be administered can vary within a wide range, for example between approximately 0.01 and approximately 10 mg per kg of body weight, preferably between 0.1 and 2 mg per kg of body weight.

The invention is described below by means of several examples which do not limit but rather illustrate the invention.

EXAMPLES

The following examples describes the production and characterization of nanoparticles based on a biodegradable polymer (PVM/MA) incorporating a cyclodextrin (Examples 1-5) and of nanoparticles based on a biodegradable polymer (PVM/MA) incorporating a cyclodextrin and a biologically active molecule (Examples 6 and 7) which is associated to the cyclodextrin and/or to the biodegradable polymer (PVM/MA) forming the matrix of said nanoparticles. Said examples show the capacity of said nanoparticles to develop bioadhesive interactions with the mucosa and to promote the oral absorption of a biologically active molecule, such as paclitaxel. As can be observed in said examples, when paclitaxel is used as a biologically active molecule, its incorporation in said nanoparticles based on PVM/MA incorporating a cyclodextrin, particularly 2-hydroxypropyl-β-cyclodextrin, allows obtaining constant and sustained plasma levels of said drug substance for at least 24 hours.

The general methods used for producing and characterizing said nanoparticles are described below.

A. Production of Nanoparticles Containing Cyclodextrins and, Optionally, a Biologically Active Molecule The process for producing nanoparticles based on a biodegradable polymer (PVM/MA) incorporating a cyclodextrin and, optionally, a biologically active molecule, is a modification of a previously described general process based on the controlled desolvation of the polymer [Arbos et al., J. Control. Release, 83 (2002) 321-330]. To that end, a methyl vinyl ether and maleic anhydride (PVM/MA) copolymer and a certain amount of cyclodextrin, or, alternatively, of a cyclodextrin:biologically active molecule complex, obtained by conventional methods (e.g. Hamada et al., J Biosci Bioeng 102(4):369-71, 2006), in acetone under magnetic stirring. After incubation, a miscible organic solvent (ethanol) and a similar volume of deionized water are added on this phase and under magnetic stirring, giving rise to the formation of the nanoparticles under the appearance of a milky suspension. The organic solvents (ethanol and acetone) are then removed by means of evaporation under reduced pressure, the particles remaining in a stable aqueous suspension. The formed nanoparticles can optionally be coated with a water-soluble biologically active molecule or with a ligand which can confer specific targeting properties to the resulting nanoparticle. After allowing the nanoparticle suspension to homogenize, it is evaporated under reduced pressure, for example by means of using a rotary evaporator, such as a Büchi R-144 rotary evaporator (Switzerland), until eliminating both organic solvents. The suspension is subsequently subjected to purification by ultracentrifugation (Sigma 3k30, rotor No.-12150, Germany) or by means of tangential filtration, and the nanoparticles can possibly be frozen at −80° C. for their subsequent lyophilization and long-term preservation (Virtis Genesis, New York, United States).

B. Physicochemical Characterization of the Nanoparticles

The characterization of the nanoparticles has entailed several studies, which are described below. Among the physicochemical studies, the particle size and the surface charge of the nanoparticles were determined, the latter by means of measuring the zeta potential. Both parameters were obtained by photon correlation spectroscopy, using a Zetasizer nano Z-S (Malvern Instruments/Optilas, Spain).

The yield of the process was calculated by two methods. In the first method, the yield was calculated gravimetrically, using the weight of the lyophilized samples without cryoprotective agent, according to Equation 1:

Yield=(Weight of the lyophilizate/Initial weight)×100 [Equation 1]

where
    the initial weight is the weight of the biodegradable polymer (e.g. PVM/MA) and of the cyclodextrin added to the formulations; and
    the weight of the lyophilizate is the weight of the formulations after the lyophilization process.

The second method was based on the quantification by means of high-performance liquid chromatography (HPLC) coupled to an ELSD (evaporative light-scattering detection)-type detector (Agueros et al., J. Pharm. and Biomed. Anal., 39 (2005) 495-502) by means of the method described below which allows quantifying the cyclodextrins and the PVM/MA copolymer. In this case, the yield was calculated according to Equation 2:

$$\text{Yield} = (Q_{initial} - Q_{PVM/MA}) \times 100 \quad \text{[Equation 2]}$$

where $Q_{initial}$ is the initial amount of PVM/MA added; and
$Q_{PVM/MA}$ is the amount of PVM/MA determined in the supernatants.

The morphology of the nanoparticles was observed by scanning electron microscopy (Zeiss, DSM 940A Germany). To that end, the lyophilized nanoparticles were coated with a molecular gold layer of about 9 nm (Emitech K550 Equipment, Sputter-Coater, United Kingdom) and the photographs were made with a Zeiss DMS 940 A microscope (United States).

To confirm the presence of cyclodextrins associated to the nanoparticles (quantification method described below), the elemental analysis of the different formulations of nanoparticles was carried out, using a LECO CHN-900 model elemental analyzer (LECO Corporation, United States).

Quantification of the Amount of Cyclodextrin Associated with the Nanoparticles

To determinate the amount of non-aminated cyclodextrin [e.g. β-cyclodextrin (β-CD) and 2-hydroxypropyl-β-cyclodextrin (OH-β-CD)] associated to the nanoparticles, a method of HPLC coupled to an ELSD-type detector was used. The analysis was conducted in a 1100 series LC model chromatograph (Agilent, Waldbornn, Germany) and the data was analyzed in a Hewlett-Packard computer by means of the Chem-Station G2171 program (Agueros et al., J. Pharm. and Biomed. Anal., 39 (2005) 495-502).

For the sample analysis, the supernatants obtained after the purification process of the nanoparticles were diluted up to 10 ml with purified water. After adding the internal standard (PEG 6000), 1 ml aliquots of supernatant were taken as a sample. The samples were analyzed using a Zorbax Eclipse XDB-Phenyl column (Agilent 150 mm×2.1 mm) and a mixture of water/acetonitrile in a gradient (see Table 1) as a mobile phase at a flow of 0.25 ml/min.

TABLE 1

Gradient conditions for the mobile phase (A: acetonitrile; B: water)

| Time (min) | A (%) | B (%) |
|---|---|---|
| 0 | 0 | 100 |
| 2 | 0 | 100 |
| 9 | 60 | 40 |
| 11 | 71 | 29 |
| 12 | 0 | 100 |

The conditions of the detector (ELSD) were optimized until achieving the maximum sensitivity according to the gradient used in the mobile phase (Nebulizer Temperature: 115° C.; Nitrogen Flow: 3.2 ml/min). The chromatographic separation of the different cyclodextrins, of PVM/MA and of the internal standard (PEG 6000) was carried out in less than 15 minutes. The retention times were:

1.08±0.05 minutes for PVM/MA;
4.58±0.07 minutes for β-CD;
10.27±0.06 for OH-β-CD; and
13.60±0.04 minutes for the internal standard.

The limit of quantification was 0.2 mg/ml for the cyclodextrins and 0.05 mg/ml for the polymer (PVM/MA). The accuracy did not exceed the limit of 7%.

In the case of the quantification of aminated cyclodextrin [e.g. 6-monodeoxy-6-monoamino-β-cyclodextrin (NH-β-CD)] associated to the nanoparticles, a variant of the above described method was used to prevent the overlapping of the peaks of the cyclodextrin and the polymer. Therefore, the samples were analyzed using an $NH_2$-Zorbax column (Agilent 4.6×150 mm, 5 μm), heated to 40° C. and a mixture of methanol/water (80/20 v/v) as a mobile phase at a flow of 1 ml/min. The conditions of the detector (ELSD) were the following: Nebulizer Temperature: 71° C. and Nitrogen Flow: 1.9 ml/min. The chromatographic separation of 6-monodeoxy-6-monoamino-β-cyclodextrin was carried out in less than 7 minutes. The retention time was 3.8±0.07 minutes.

Finally, the amount of cyclodextrin (CD) associated to the nanoparticles was calculated as the difference between the amount of CD initially added and the amount of CD quantified in the supernatants.

Quantification of RBITC

The amount of rhodamine B isothiocyanate (RBITC) incorporated in the nanoparticles was determined by colorimetry at a wavelength of 540 nm (Labsystems iEMS Reader MF, Finland). For this quantification, calibration curves of RBITC in 0.1 N NaOH in a range of 5-50 μg/ml; r=0.999, were used.

The amount of RBITC was estimated as the difference between the initial amount added and the amount found after total hydrolysis of a certain amount of nanoparticles in 0.1N NaOH (24 h, 37° C.).

Release of RBITC

The kinetics of release of RBITC from the nanoparticles was carried out in Vivaspin® 100,000 MWCO dialysis tubes (VIVASPIN, Hannover, Germany). To that end, 10 mg of nanoparticles were dispersed in 1 ml of simulated gastric medium (0-1 h) or simulated intestinal medium (1 to 24 h) (USP XXIII) at 37±1° C. At certain times, the suspensions of nanoparticles were centrifuged (5,000×g, 15 min) and the amount of RBITC in the filtrates was quantified by colorimetry (λ=540 nm).

Quantification of Paclitaxel

The amount of paclitaxel encapsulated in the nanoparticles was determined by HPLC. The analysis was carried out in a 1100 series LC model chromatograph (Agilent, Waldbornn, Germany) coupled to a diode-array UV detection system. The data was analyzed in a Hewlett-Packard computer through the Chem-Station G2171 program. For the separation of paclitaxel a Phenomenex Gemini C18 reversed-phase column (150 mm×3 mm; 5 μm) heated to 30° C. was used. The mobile phase was formed by a mixture of phosphate regulating solution (pH=2; 0.01 M) and acetonitrile (in a 50/50 ratio by volume), and was pumped at a flow of 0.5 ml/min. The detection was carried out at 228 nm.

For the fresh sample analysis, 100 μl of the aqueous nanoparticle suspension were taken and broken with 100 μl of acetonitrile. The solvents were evaporated (centrifuge-evaporator) and the sample was reconstituted in the mobile phase used. 100 μl aliquots were injected in the HPLC column for their analysis.

C. Bioadhesion Studies

Bioadhesion studies were conducted using the previously described protocol [Arbos et al., Int. J. Pharm., 242 (2002) 129-136], according to the rules of the Ethics Committee of the University of Navarra and to the European legislation on experimental animals (86/609/EU).

To that end, male Wistar male rats with an average weight of 225 g (Harlan, Spain) were kept under normal conditions without food and water. 1 ml of aqueous suspension containing 10 mg of nanoparticles labeled with RBITC was orally administered to the animals. The animals were sacrificed at different times (0.5, 1, 3 and 8 hours) by means of cervical dislocation. The abdominal cavity was opened and the gastrointestinal tract was removed and divided into six anatomical regions: stomach (Sto), small intestine (I1, I2, I3 and I4) and cecum (Ce). Each mucosa segment was longitudinally opened and rinsed with PBS (pH 7.4). Each of these parts was in turn cut into five similar portions and the tissue was digested with 1 ml of 3 M NaOH for 24 hours. 2 ml of methanol were used to extract the rhodamine, it was stirred for 1 minute with the vortex and then centrifuged at 2,000×g for 10 minutes (5804R Centrifuge, Rotor A-4-44, Germany). 1 ml aliquots of the obtained supernatants were diluted with water (3 ml) and were analyzed by spectrofluorimetry at $\lambda_{ex}$ 540 nm and $\lambda_{em}$ 580 nm (GENios, Austria) to estimate the nanoparticle fraction adhered to the mucosa. The calibration lines were prepared by means of adding solutions of RBITC in 3 M NaOH (0.5-10 µg/ml) to control tissue segments, which were subjected to the same extraction steps (r>0.996).

In order to compare the different formulations, the bioadhesion kinetics and curves were studied. To that end, the adhered nanoparticle fraction was plotted against time, thus obtaining the bioadhesion curves. Based on the latter, and using the WinNonlin 1.5 computer application (Pharsight Corporation, United States), the following kinetic bioadhesion parameters were determined: $Q_{max}$, $AUC_{adh}$, $T_{max}$, $MRT_{adh}$ and $K_{adh}$ (Arbos et al., J. Control. Release, 89 (2003) 19-30). $Q_{max}$ (mg) is the initial maximum capacity of nanoparticles adhered to the gastrointestinal mucosa and is related to their capacity to develop bioadhesive interactions. $AUC_{adh}$ (mg·h) is the area under the curve of the adhered nanoparticle fraction and represents the bioadhesion intensity. $MRT_{adh}$ (h) is the estimated mean time that the formulations remain adhered to the mucosa. $K_{adh}$ is defined as the rate of elimination of the fraction adhered in the mucosa. All these parameters were estimated between 0 and 8 hours. The calculations were carried out using the WinNonlin 1.5 program (Pharsight Corporation, USA).

D. Viewing of the Nanoparticles Adhered to the Mucosa

The viewing of the nanoparticles containing cyclodextrins and, optionally, a biologically active molecule, in the gastrointestinal mucosa was observed by fluorescence microscopy. To that end, the formulations containing RBITC were used. Said formulations (10 mg of nanoparticles) were administered orally to the laboratory animals (male Wistar rats) which were sacrificed two hours later. After the sacrifice, the gastrointestinal tract was extracted, collecting different portions of the small intestine which were washed with phosphate buffered saline (pH=7.4; 0.15 M), as has been previously described for the bioadhesion studies. The different intestinal sections were treated with O.C.T.™ (Sakura, Netherlands) and frozen in liquid nitrogen. The tissue samples were subsequently cut into 5 µm-thick sections in a cryostat (2800 Frigocut E, Reichert-Jung, Germany), and fixed to supports for viewing them by fluorescence microscopy.

E. Pharmacokinetic Studies

The pharmacokinetic studies were conducted according to the rules of the Ethics Committee of the University of Navarra as well as of the European legislation on experimental animals (86/609/EU). To that end, male Wistar rats with an average weight of 225 g (Harlan, Spain) were isolated in metabolic cages 12 hours before administering the formulations, without access to food, but allowing them free access to drinking water.

The animals were divided into 8 treatment groups (6 animals per group) and were treated with single doses of 10 mg/kg (2.25 mg) of paclitaxel incorporated in any of the following formulations:

(i) i.v. solution of Taxol® (Bristol-Myers Squibb, Madrid, Spain);
(ii) oral solution of Taxol®;
(iii) paclitaxel (PTX)-2-hydroxypropyl-β-cyclodextrin (OH-β-CD) [PTX-OH-β-CD] complex;
(iv) paclitaxel (PTX)-β-cyclodextrin (β-CD) [PTX-β-CD] complex;
(v) paclitaxel (PTX)-6-monodeoxy-6-monoamino-β-cyclodextrin (NH-β-CD) [PTX-NH-β-CD] complex;
(vi) paclitaxel (PTX)-2-hydroxypropyl-β-cyclodextrin (OH-β-CD)-nanoparticle based on PVM/MA (NP) [PTX-OH-β-CD-NP] complex;
(vii) paclitaxel (PTX)-β-cyclodextrin (β-CD)-nanoparticle based on PVM/MA (NP) [PTX-β-CD-NP] complex; and
(viii) paclitaxel (PTX)-6-monodeoxy-6-monoamino-β-cyclodextrin-nanoparticle based on PVM/MA (NP) [PTX-NH-β-CD-NP] complex.

1 ml of the different formulations, dissolved or dispersed in water, was administered to the animals, except in the case of the i.v. solution (commercial formulation), which was administered in the tail vein (0.3 ml).

After the administration, a volume of blood of approximately 300 µl was extracted at different times, using ethylenediaminetetraacetic acid (EDTA) as an anticoagulant and recovering the blood volume of the animal (rat) with an equivalent volume of physiological saline by an intraperitoneal (i.p.) route. The blood was centrifuged at 5,000 rpm for 10 minutes and the supernatant (plasma) was frozen at a temperature of −80° C. The study was conducted according to the principles included in the international guidelines for animal experimentation (WHO Chronicle, 39 (2): 51-56, 1985; A CIOMS Ethical Code for Animal Experimentation) by means of the protocol approved by the Ethics Committee of animal experimentation of the University of Navarra.

Pretreatment of the Samples

The extraction of paclitaxel from plasma was carried out by means of a liquid-liquid extraction process, using t-butylmethylether as an extraction solvent. To that end, plasma aliquots (0.1 ml) were taken, adjusted to a volume of 1 ml with water and 0.2 µg of docetaxel as an internal standard were added to them. Then, 4 ml of tert-butylmethylether were added and they were stirred for 1 minute. The samples were then centrifuged at 10,000 rpm for 10 minutes and the supernatant (organic phase) was collected and evaporated in a centrifuge evaporator (Savant, Barcelona, Spain). The extract thus obtained was reconstituted in 200 µl of a mixture (50/50 v/v) of acetonitrile and phosphate regulating solution (pH=2; 0.01 M) by means of stirring with a vortex for 1 minute. The resulting solution was transferred to an injection vial.

Analytical Method: HPLC

The quantification of paclitaxel was carried out by high-performance liquid chromatography (HPLC) with ultraviolet-visible detection. docetaxel was used as an internal standard. The analysis was carried out in a 1100 series LC model chromatograph (Agilent, Waldbornn, Germany). The data was analyzed in a Hewlett-Packard computer by means of the Chem-Station G2171 program. For the separation of paclitaxel, a Gemini C18 reversed-phase column (Phenomenex) 150 mm×3 mm; 5 µm, heated to 30° C., was used. The mobile phase was formed by a mixture of phosphate regulating solution (pH=2; 0.01 M) and acetonitrile (in a 50/50 ratio by volume), and was driven through the column at a flow of 0.5 ml/min. The detection was carried out at 228 nm.

The analytical method used was validated, the lineal relationship between the response of the detector and the plasma concentrations of paclitaxel throughout the range of concentrations comprised between 40 and 3,200 ng/ml being verified.

Pharmacokinetic Analysis

The pharmacokinetic analysis of the plasma concentration data over time obtained after administering paclitaxel was carried out using the non-compartmental adjustment process of the WiNNonlin 1.5 pharmacokinetic adjustment program (Pharsight Corporation, Mountain View, United States).

The following pharmacokinetic parameters were calculated: the maximum concentration ($C_{max}$); the time at which the $C_{max}$ ($t_{max}$) is reached; the area under the plasma level curve (AUC0-inf); the mean residence time (MRT) and the biological half-life in the terminal elimination phase ($t_{1/2z}$), clearance (Cl) and the steady-state distribution volume.

The mean residence time (MRT) was calculated by means of the ratio between the value of AUMC (area under the curve at the first moment of the plasma concentration) and that of AUC. The clearance (Cl) was calculated as Dose×Bioavailability/AUC, and the steady-state distribution volume (Vss) was calculated as the ratio between the clearance and the terminal elimination constant (k), calculated as 1/MRT.

F. Statistical Analysis

For the bioadhesion and pharmacokinetics study, the formulations were analyzed using the non-parametric "Mann-Whitney" test. Values of P<0.05 were considered significant. All the calculations were carried out with the SPSS® statistical software program (SPSS® 10, Microsoft, United States).

Example 1

Optimization of the Process of Association Between a Biodegradable Polymer (PVM/MA) and a Cyclodextrin for Obtaining Nanoparticles The nanoparticles were prepared by controlled desolvation after the modification of a previously described process [Arbos et al., J. Control. Release, 83 (2002) 321-330]. To that end, the methyl vinyl ether and maleic anhydride (PVM/MA) copolymer and a certain amount of β-cyclodextrin (β-CD), 2-hydroxypropyl-β-cyclodextrin (OH-β-CD) or 6-monodeoxy-6-monoamino-β-cyclodextrin (NH-β-CD) were incubated in acetone under magnetic stirring. After incubation, a miscible organic solvent (ethanol) and a similar volume of deionized water were added on this phase and under magnetic stirring, giving rise to the formation of the nanoparticles under the appearance of a milky suspension. After allowing the nanoparticle suspension to homogenize, it was evaporated under reduced pressure (Büchi R-144 rotary evaporator, Switzerland) until eliminating both organic solvents. the suspension was subsequently purified by ultracentrifugation (Sigma 3k30, rotor No.-12150, Germany). A part of the obtained nanoparticles was frozen at −80° C. for their subsequent lyophilization and long-term preservation (Virtis Genesis, New York, United States).

FIG. 1 shows the amount of cyclodextrin associated to the nanoparticles according to the incubation time with the biodegradable polymer (PVM/MA) while preparing the nanoparticles. In all cases, a optimal incubation time between the CD and the polymer was observed. This incubation time was 30 minutes. Finally, it must be emphasized that β-CD associates more efficiently to the PVM/MA nanoparticles than its hydroxylated (OH-β-CD) or aminated (NH-β-CD) derivative.

According to the results obtained, the following experimental conditions were selected for subsequent studies:
cyclodextrin:PVM/MA copolymer (1:4) ratio; and
incubation time of 30 minutes.

Example 2

Production of Nanoparticles Containing Cyclodextrins 2.1 Production of Nanoparticles Containing Cyclodextrins The nanoparticles were prepared by controlled desolvation after the modification of a previously described process [Arbos et al., J. Control. Release, 83 (2002) 321-330]. To that end, 25 mg of β-CD, OH-β-CD or NH-β-CD were dispersed in 2 ml of acetone with the aid of ultrasound (Microson™ or in an ultrasound bath for 1 minute under cooling). This suspension was added to a solution of 100 mg of methyl vinyl ether and maleic anhydride (PVM/MA) copolymer [Gantrez® AN 119] in 3 ml of acetone and the mixture was allowed to incubate for 30 minutes. Subsequently, 10 ml of ethanol and 10 ml of deionized water were added on this phase and under magnetic stirring. The resulting mixture was allowed to homogenize for 5 minutes. The nanoparticle suspension was then evaporated under reduced pressure (Büchi R-144, Switzerland) until eliminating both organic solvents and the final volume was adjusted with water to 10 ml. The suspension was subsequently subjected to purification by ultracentrifugation (20 minutes at 27,000× g) (Sigma 3k30, rotor No.-12150, Germany). The supernatants were eliminated and the residue was resuspended in water or in a 5% aqueous solution of sucrose. Possibly, part of the obtained nanoparticles was frozen at −80° C. for their subsequent lyophilization and long-term preservation (Virtis Genesis, New York, United States).

2.2 Physicochemical Characterization of the Different Obtained Nanoparticles Based on PVM/MA Containing Cyclodextrins The determination of the physicochemical characteristics allowed verifying how, independently of the CD used, the nanoparticles have similar sizes and surface charges. Furthermore, this charge was similar to that of the non-treated nanoparticles, it can therefore be considered that most of the CD is located inside the nanoparticles and not adsorbed on their surface. Table 2 summarizes the main physicochemical characteristics of the nanoparticles analyzed.

TABLE 2

Physicochemical characteristics of the different formulations of nanoparticles based on PVM/MA containing cyclodextrins

| Formulation | Size (nm) | Zeta potential (mV) | Yield (%) | Associated CD (μg/mg) | Association Efficiency (%) |
|---|---|---|---|---|---|
| NP | 179 ± 2 | −48.1 ± 0.8 | 91.3 ± 3.1 | — | — |
| β-CD - NP | 144 ± 6 | −51.1 ± 8.8 | 94.4 ± 5.3 | 88.4 ± 9.9 | 30.2 ± 7.8 |
| OH-CD - NP | 140 ± 7 | −52.1 ± 3.7 | 91.1 ± 4.1 | 68.4 ± 4.3 | 22.8 ± 4.7 |
| NH-CD - NP | 151 ± 7 | −49.3 ± 2.4 | 86.2 ± 3.9 | 71.2 ± 8.4 | 25.4 ± 5.4 |

The data shown the mean ± the standard deviation (SD) (n = 12).
Experimental condidtions: PVM/MA: 100 mg; cyclodextrin: 25 mg; incubation time: 30 min.
The data shown the mean ± (n = 12).
NP: nanoparticles based on PVM/MA without cyclodextrin.

As can be seen in Table 2, independently of the cyclodextrin used, the nanoparticles have similar sizes and surface charges. Furthermore, this charge was similar to that of the non-treated nanoparticles, it can therefore be considered that most of the cyclodextrin is located inside the nanoparticles and not adsorbed on their surface. The association between the cyclodextrins and the nanoparticles based on PVM/MA allows obtaining nanoparticles with a size smaller than conventional nanoparticles (NP). As shown in Table 2, the nanoparticles based on PVM/MA containing cyclodextrins show a size close to 150 nm. This decrease in the size could be associated to the high yield of the process for manufacturing the nanoparticles. These yields were obtained by means of determining their weight at the end of the process and after their lyophilization. The manufacturing yields are expressed in percentage, calculated in relation to the initial mass of the PVM/MA copolymer and the cyclodextrin.

The amount of cyclodextrin associated to the nanoparticles varies according to the type of oligosaccharide used, being about 90 μg/mg for β-CD and 70 μg/mg for OH-β-CD and NH-β-CD. The confirmation of the presence of CD associated to the nanoparticles based on PVM/MA was carried out after the elemental analysis of the different formulations. The results obtained (Table 3) confirmed the presence of CD due to an important increase in the proportion of oxygen in the formulations having the associated CD, as well as a decrease of the percentage of carbon, compared to the control nanoparticles (NP).

TABLE 3

Results of the elemental analysis of the control (NP)
formulations and of the formulations of nanoparticles based on
PVM/MA associated to CD

| Formulation | C (%) | H (%) | O (%) | N (%) |
|---|---|---|---|---|
| NP | 52.52 | 5.09 | 42.46 | −0.07 |
| β-CD-NP | 42.37 | 5.94 | 51.61 | 0.08 |
| OH-β-CD-NP | 41.27 | 5.92 | 52.84 | −0.04 |
| NH-β-CD-NP | 43.12 | 5.78 | 51.17 | −0.07 |

NP: Control nanoparticles based on PVM/MA without CD (empty);
β-CD-NP: Nanoparticles based on PVM/MA with β-CD;
OH-β-CD-NP: Nanoparticles based on PVM/MA with OH-β-CD;
NH-β-CD-NP: Nanoparticles based on PVM/MA with NH-β-CD.

Figure 2:
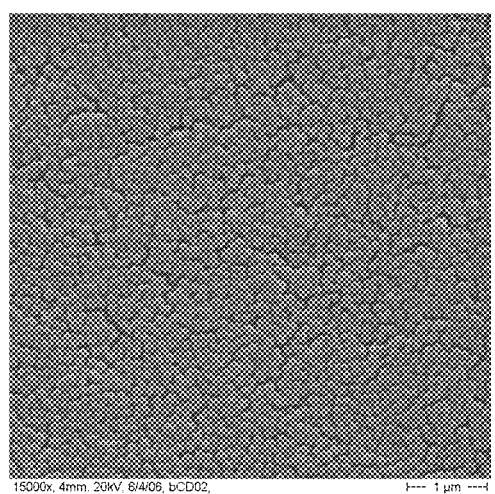
FIG. 2 is a photograph of the result obtained upon subjecting a lyophilized sample of nanoparticles based on PVM/MA with β-cyclodextrin (β-CD-NP) to scanning electron microscopy.

The morphology of the nanoparticles was observed by scanning electron microscopy (Zeiss, Germany), after which the typical spherical shape of the nanoparticles, homogeneous and with a size comprised between 80 and 200 nm, was observed. FIG. 2 shows the results of subjecting a lyophilized sample of nanoparticles based on PVM/MA with β-CD (β-CD-NP) to scanning electron microscopy.

Example 3

Production of Nanoparticles Containing
Cyclodextrins and RBITC

The nanoparticles were prepared by controlled desolvation after the modification of a previously described process [Arbos et al., J. Control. Release, 83 (2002) 321-330]. To that end, 25 mg of β-CD, OH-β-CD or NH-β-CD were dispersed in 2 ml of acetone with the aid of ultrasound (Microson™ or in an ultrasound bath for 1 minute under cooling). This suspension was added to a solution of 100 mg of methyl vinyl ether and maleic anhydride (PVM/MA) copolymer [Gantrez® AN 119] in 3 ml of acetone and the mixture was allowed to incubate for 30 minutes. Subsequently, 10 ml of ethanol and 10 ml of deionized water were added on this phase and under magnetic stirring. The resulting mixture was allowed to homogenize for 5 minutes. The nanoparticle suspension was then evaporated under reduced pressure (Büchi R-144, Switzerland) until eliminating both organic solvents and the final volume was adjusted with water to 10 ml. An aqueous solution of rhodamine B isothiocyanate (RBITC) was then added to the nanoparticles and it was allowed to incubate for 5 minutes at room temperature and with magnetic stirring. The suspension was subsequently subjected to purification by ultracentrifugation (20 minutes at 27,000×g) (Sigma 3k30, rotor No.-12150, Germany). The supernatants were eliminated and the residue was resuspended in water or in a 5% aqueous solution of sucrose. Possibly, part of the obtained nanoparticles was frozen at −80° C. for their subsequent lyophilization and long-term preservation (Virtis Genesis, New York, United States).

The amount of RBITC was estimated as the difference between the initial amount added and the amount found after total hydrolysis of a certain amount of nanoparticles in 0.1 N NaOH (24 h, 37° C.). Table 4 shows the values of RBITC (μg of RBITC/mg of nanoparticle) for the different assayed formulations.

TABLE 4

RBITC (μg/mg) associated to the nanoparticles

| Formulation | Size (nm) | RBITC (μg/mg) |
|---|---|---|
| NP | 179 ± 2 | 10.9 ± 0.3 |
| β-CD-NP | 144 ± 6 | 13.3 ± 2.1 |
| OH-β-CD-NP | 140 ± 7 | 12.4 ± 1.3 |
| NH-β-CD-NP | 151 ± 7 | 11.8 ± 0.7 |

The data shows the mean ± SD (n = 8).
Experiment condtions: PVM/MA: 100 mg; cyclodextrin: 25 mg; incubation time: 30 min.
NP: Control nanoparticles based on PVM/MA without CD (empty).
β-CD-NP: Nanoparticles based on PVM/MA with β-CD.
OH-β-CD-NP: Nanoparticles based on PVM/MA with OH-β-CD.
NH-β-CD-NP: Nanoparticles based on PVM/MA with NH-β-CD.

Figure 3:
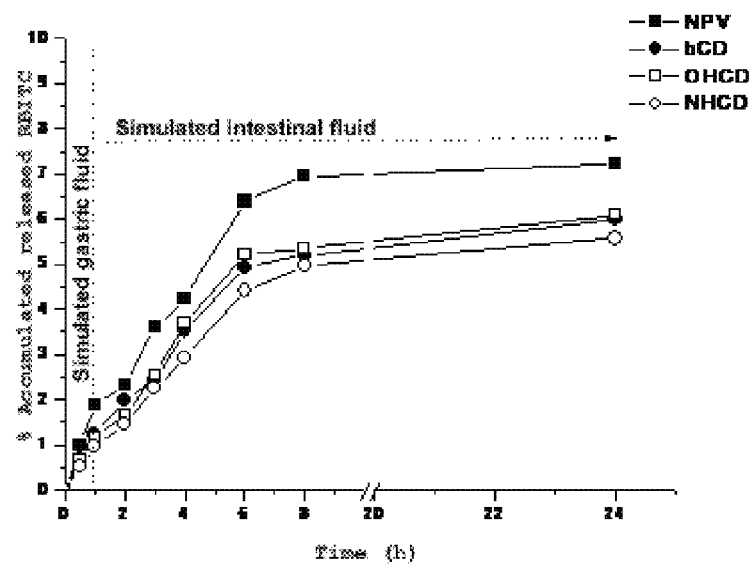
FIG. 3 is a graph that shows the release of RBITC from nanoparticles containing cyclodextrins (β-CD-NP: nanoparticles based on PVM/MA with β-CD; OH-β-CD-NP: nanoparticles based on PVM/MA with OH-β-CD; NH-β-CD-NP: nanoparticles based on PVM/MA with NH-β-CD) and from control nanoparticles (NP) after their incubation in simulated gastric medium (during the first hour: 0-1 h) and in simulated intestinal medium (1 to 24 h) at 37±1° C. The data shows the mean±standard deviation (n=3).

FIG. 3 shows the kinetics of release of RBITC from the nanoparticles in simulated gastric medium (0-1 h) and in simulated intestinal medium (1 to 24 h) at 37±1° C. In all cases, it was verified that the percentage of RBITC released after 24 hours of incubation was always less than 10% of the amount associated to the nanoparticles. It can therefore be assumed that the results obtained in subsequent bioadhesion studies as well as in the fluorescence microscopy, the fluorescence intensity corresponds to the RBITC associated to the nanoparticles.

Example 4

Figure 4:
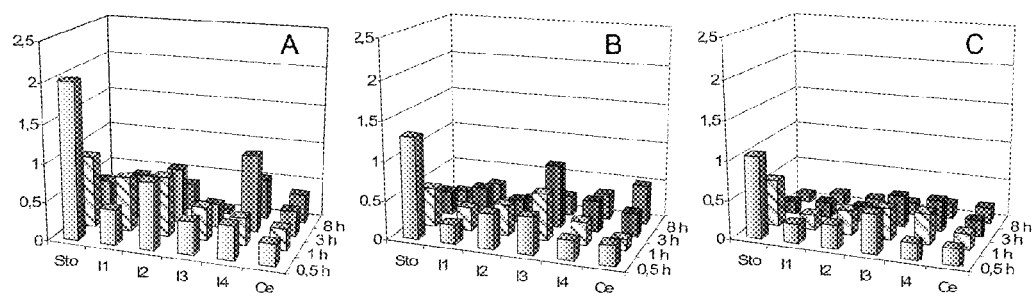
FIG. 4 shows a bar graph representing the distribution of (A) nanoparticles based on PVM/MA with hydroxypropyl-β-CD (OH-β-CD-NP); (B) nanoparticles based on PVM/MA with β-CD; and (C) control nanoparticle (NP), in the gastrointestinal tract mucosa after oral administration of 10 mg of nanoparticles fluorescently labeled with RBITC. The x-axis represents the different mucosa segments; the y-axis represents the nanoparticle fraction adhered to the mucosa; and the z-axis represents the time after administration.

Evaluation of the Bioadhesive Characteristics of the
Nanoparticles Containing Cyclodextrins in the
Gastrointestinal Tract of Rats FIG. 4 shows the bioadhesion profile of the assayed formulations, representing the adhered nanoparticle fraction in the different gastrointestinal tract segments (stomach; small intestine: I1-I4; cecum) after 30 minutes, 1 h, 3 h and 8 h after oral administration, according to the previously described methodology. As can be observed in said figure, the nanoparticles associated to cyclodextrins showed a bioadhesion profile different from that of the control nanoparticles. In recent works, the bioadhesive potential of the PVM/MA copolymer proved to be much higher when incorporated in the nanoparticles than when it was administered in the form of a simple aqueous solution (Arbos et al., J. Control. Release, 89 (2003) 19-30). This fact agrees with previous works which suggested that the shape of the nanoparticle would facilitate both the initial contact and the adhesive interactions with the components of the mucosa.

Thirty minutes after the administration, all the assayed formulations showed a bioadhesion maximum in the stomach and in the jejunum (portion I2 in FIG. 4). In any case, a greater interaction with the nanoparticles associated to OH-β-CD seems to be observed. Therefore, 30 minutes after the administration, it can be stated that about 12-20% of the administered dose of the formulations is adhered to the stomach and approximately between 14-22% in the small intestine. Said values are significantly different to those found for conventional nanoparticles (based on PVM/MA) without CD, in which less than 10% and no more than 12% of the administered dose is adhered to the stomach and small intestine, respectively.

One hour after the administration, it can be observed how the nanoparticle fraction with cyclodextrins adhered to the gastrointestinal mucosa decreases and moves to distal portions of the tract. In any case, it can be observed that said distribution is homogeneous and no formulation shows specificity for any region of the gastrointestinal tract.

Figure 5:
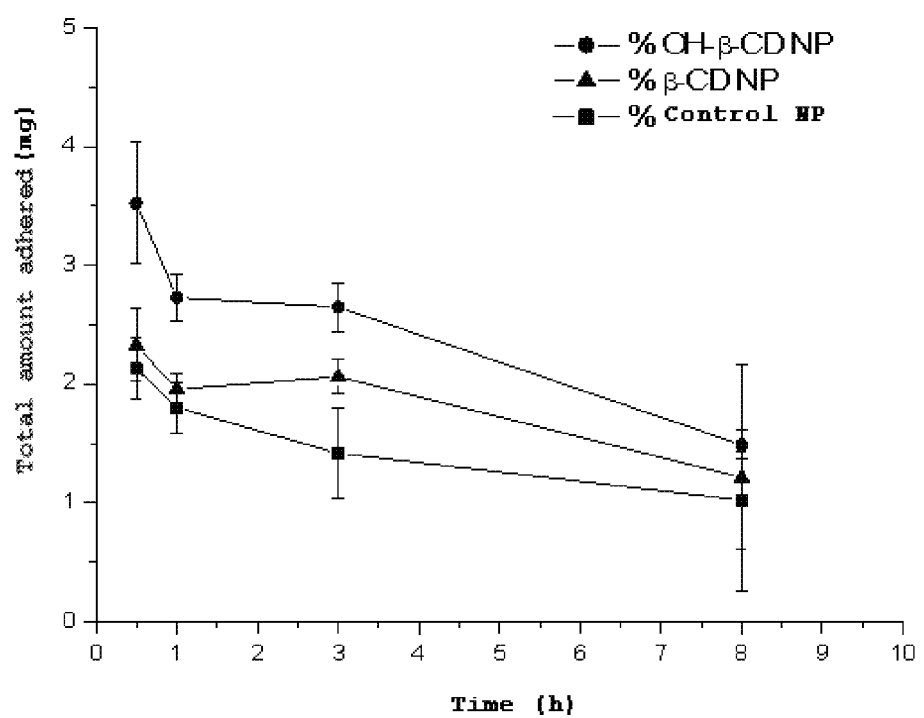
FIG. 5 is a graph showing the bioadhesion curves obtained upon representing the nanoparticle fraction adhered in the entire gastrointestinal tract with respect to time. The represented formulations are (●) OH-β-CD-NP; (▲) β-CD-NP; and (■) Control NP. The values represent the mean±standard deviation (n=3).

In order to compare the adhesive potential of the different formulations, the bioadhesion kinetics and curves were studied. To that end, the adhered nanoparticle fraction was plotted against time, thus obtaining the bioadhesion curves. These curves are shown in FIG. 5. Based on the latter, and using the WinNonlin 1.5 computer application (Pharsight Corporation, United States), the following kinetic bioadhesion parameters were determined: $Q_{max}$, $AUC_{adh}$, $T_{max}$, $MRT_{adh}$ and $K_{adh}$ (Arbos et al., J. Control. Release, 89 (2003) 19-30). Table 5 shows these parameters.

TABLE 5

Bioadhesion parameters for the different formulations of nanoparticles

| | $Q_{max}$ (mg) | $AUC_{adh}$ (mg · h) | $K_{adh}$ (h$^{-1}$) | MRT (h) |
|---|---|---|---|---|
| OH-β-CD-NP | 3.5 ± 0.5** | 18.16 ± 4.47* | 0.098 ± 0.084** | 3.4 ± 0.41* |
| β-CD-NP | 2.3 ± 0.3 | 13.86 ± 1.03 | 0.077 ± 0.029** | 3.5 ± 0.10* |
| NP | 2.1 ± 0.2 | 10.49 ± 2.10 | 0.292 ± 0.03 | 2.7 ± 0.23 |

The results are expressed as mean ± SD (n = 3).
*$p < 0.05$ OH-β-CD-NP and β-CD-NP vs. NP.
**$p < 0.01$ OH-β-CD-NP and β-CD-NP vs. NP.
$Q_{max}$ (mg): maximum amount of nanoparticles adhered to the mucosa.
$AUC_{adh}$ (mg · h): area under the bioadhesion curve.
$K_{adh}$ (h$^{-1}$): rate of elimination of the adhered fraction.
$MRT_{adh}$ (h): mean residence time of the adhered nanoparticle fraction.
OH-β-CD-NP: Nanoparticles based on PVM/MA with OH-β-CD.
β-CD-NP: Nanoparticles based on PVM/MA with β-CD.
NP: Control nanoparticles based on PVM/MA without CD (empty).

As can be seen, the nanoparticles associated to OH-β-CD are characterized by an $AUC_{adh}$ (a parameter measuring the intensity of the bioadhesive interactions) which is 1.5 times greater than that observed for the control nanoparticles (NP). Likewise, the adhered fraction of the formulations associated to cyclodextrins showed a rate of elimination ($K_{adh}$) significantly lower than that of the control NP ($p<0.01$) and a mean residence time ($MRT_{adh}$) of approximately 3.5 hours. These results allow assuming that the presence of cyclodextrins (especially OH-CD) can facilitate the interaction with the gastrointestinal mucosa and develop adhesive interactions with components of the mucosa stronger than the NP.

Example 5

Figure 6:
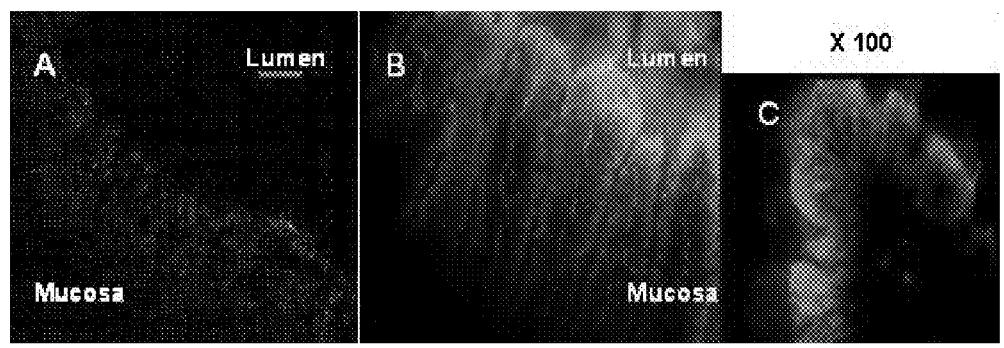
FIG. 6 is a set of photographs showing the viewing by fluorescence microscopy of the control nanoparticles (A) and OH-β-CD-NP (B, C) adhered to rat ileum after 2 hours of the oral administration of a single dose of 10 mg.

Viewing the Nanoparticles Containing Cyclodextrins in the Gastrointestinal Mucosa The viewing of the distribution of the nanoparticles associated to cyclodextrins in the gastrointestinal mucosa was observed by fluorescence microscopy. To that end, the different formulations labeled with RBITC were administered to laboratory animals. Two hours after their administration, the animals were sacrificed and different portions of the small intestine were examined. FIG. 6 shows some photographs which allow observing the distribution of the nanoparticles in ileum samples.

In accordance with the in vivo bioadhesion studies, the nanoparticles associated to hydroxypropyl-β-cyclodextrin have a greater capacity to establish bioadhesive interactions with the mucosa than the control nanoparticles. The conventional nanoparticles were not able to reach the enterocytes in spite of their ability to penetrate in the mucus layer lining the mucosa. On the contrary, the nanoparticles associated to cyclodextrin were significantly adhered in the enterocytes of the intestine.

Example 6

Nanoparticles with Cyclodextrins Comprising Paclitaxel

The process for manufacturing nanoparticles containing cyclodextrins with paclitaxel is divided into two different steps:

1) Production of the paclitaxel-cyclodextrin complex, including both the formation and the purification of the formed complex; and
2) Production of nanoparticles containing the paclitaxel-cyclodextrin complex.

Production of the Paclitaxel-Cyclodextrin Complex

For this purpose, an aqueous solution of cyclodextrin (β-CD, OH-β-CD or NH-β-CD) was prepared which was added on an ethanol solution of the paclitaxel (PTX) drug in an 80:20 (v:v) ratio, and with a drug:cyclodextrin (1:1) molar ratio. The mixture was maintained under magnetic stirring (300 rpm) in the dark and at room temperature until reaching equilibrium (at least 72 hours). The ethanol was then eliminated under evaporation under reduced pressure and the suspension was filtered (0.45 µm) to eliminate the undissolved drug crystals. Finally, the water was completely eliminated from the final aqueous solution by evaporation under reduced pressure, the paclitaxel-cyclodextrin complex remaining under the appearance of a white powder.

Production of Nanoparticles Comprising the Paclitaxel-Cyclodextrin Complex

The nanoparticles were obtained by controlled desolvation after the modification of a previously described process (Arbos et al., 2002, mentioned above). To that end, a certain amount of the complex previously formed between paclitaxel and the cyclodextrin (β-CD, OH-β-CD or NH-β-CD) was dispersed in 2 ml of acetone. This suspension was added to a solution of 100 mg of methyl vinyl ether and maleic anhydride (PVM/MA) copolymer [Gantrez® AN 119] in 3 ml of acetone and the mixture was allowed to incubate for 30 minutes. Subsequently, 10 ml of ethanol and 10 ml of deionized water were added on this phase and under magnetic stirring. The resulting mixture was allowed to homogenize for 5 minutes. The nanoparticle suspension was then evaporated under reduced pressure (Büchi R-144, Switzerland) until eliminating both organic solvents and the final volume was adjusted with water to 10 ml. The suspension was subsequently subjected to purification by ultracentrifugation (20 minutes a 27,000×g) (Sigma 3k30, rotor No.-12150, Germany). The supernatants were eliminated and the residue was resuspended in water or in a 5% aqueous solution of sucrose. Part of the obtained nanoparticles was frozen at −80° C. for their subsequent lyophilization and long-term preservation (Virtis Genesis, New York, United States).

Figure 7:
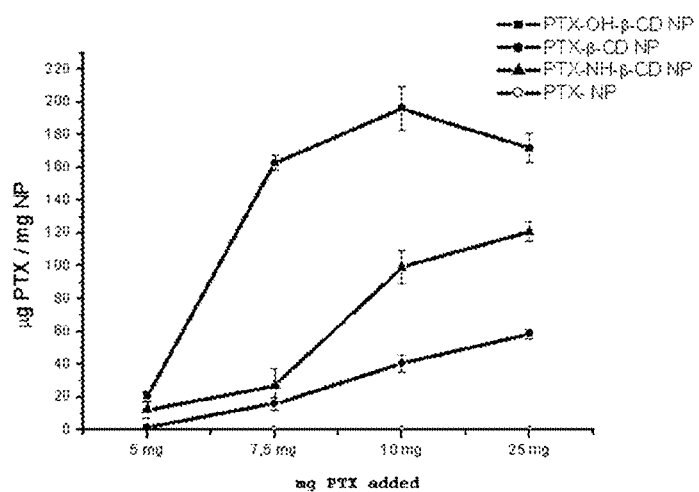
FIG. 7 is a graph showing the evolution of the amount of paclitaxel (PTX) encapsulated in different formulations according to the type of cyclodextrin used and the amount of drug initially added. The results show mean±standard deviation (n=6). PTX-NP: conventional PVM/MA nanoparticles with paclitaxel; PTX-β-CD-NP: PVM/MA and β-CD nanoparticles with paclitaxel; PTX-OH-β-CD-NP: PVM/MA and OH-β-CD nanoparticles with paclitaxel; and PTX-NH-β-CD-NP: PVM/MA and NH-β-CD nanoparticles with paclitaxel.

Optimization of the Process for Encapsulating the Paclitaxel-Cyclodextrin Complex in the Nanoparticles FIG. 7 shows the evolution of the PTX content in the nanoparticles containing cyclodextrins and PTX, according to the amount and type of cyclodextrin used. It should first be emphasized that PTX by itself, i.e. without forming a complex with the CDs, cannot be included in the nanoparticles, being eliminated in the process for purifying the nanoparticles by filtration. It is therefore necessary to form the paclitaxel-cyclodextrin (PTX-CD) complex. For the different used cyclodextrins, it was observed how the best encapsulation efficiencies were obtained when PTX forms a complex with OH-β-CD, followed by t NH-β-CD and by β-CD without substitution.

Likewise, different amounts of PTX (5, 7.5, 10 and 25 mg) were also assayed, always keeping the 1:1 molar ratio with the corresponding cyclodextrin, and it was observed that for amounts higher than 10 mg of PTX [PTX:PVM/MA (1:10)], larger amounts of encapsulated drug were not obtained, and consequently, a decrease in the encapsulation efficiency of the PTX-CD complex in the NP was observed. After these assays, it was determined that, in the assayed conditions, the optimal amount of PTX to be included in the different formulations was 10 mg, thus obtaining the best yields. Table 7 shows the amount of encapsulated PTX when 10 mg were initially added according to the different cyclodextrins used to form the complex.

TABLE 7

Amount of PTX associated to different formulations of nanoparticles according to the type of cyclodextrin used (initial amount of paclitaxel added: 10 mg)

| Formulation | Size (nm) | PTX (µg/mg) |
|---|---|---|
| PTX-NP | 204 ± 4 | 0.29 ± 0.13 |
| PTX-β-CD-NP | 298 ± 6 | 40.5 ± 5.12 |
| PTX-OH-β-CD-NP | 307 ± 7 | 171.01 ± 13.41 |
| PTX-NH-β-CD-NP | 310 ± 6 | 99.26 ± 10.13 |

The results show mean ± standard deviation (n =6).
PTX-NP: conventional PVM/MA nanoparticles with paclitaxel;
PTX-β-CD-NP: PVM/MA and β-CD nanoparticles with paclitaxel;
PTX-OH-β-CD-NP: PVM/MA and OH-β-CD nanoparticles with paclitaxel; and
PTX-NH-β-CD-NP: PVM/MA and NH-β-CD nanoparticles with paclitaxel.

Example 7

Pharmacokinetic Study after the Oral Administration of Different Paclitaxel Formulations Paclitaxel is a drug which is characterized by having a dose-dependent pharmacokinetic profile. Therefore, it was previously necessary to determine the pharmacokinetic profile after orally or intravenously administering the commercial paclitaxel formulation at the selected dose for its formulation in nanoparticles (10 mg/kg).

Pharmacokinetic studies were conducted according to the rules of the Ethics Committee of the University of Navarra as well as the European legislation on experimental animals (86/609/EU). To that end, male Wistar rats with an average weight of 225 g (Harlan, Spain) were isolated in metabolic cages 12 hours before administering the formulations, without access to food, but allowing them free access to drinking water.

TABLE 8

Physicochemical characteristics of the different formulations with paclitaxel-cyclodextrin complex used in the pharmacokinetic studies

| Formulation | Size (nm) | PDI | Zeta potential (mV) | Yield (%) | PTX (µg/mg) |
|---|---|---|---|---|---|
| PTX-NP | 204 ± 4 | 0.07 | −38.3 ± 2.1 | 51.2 ± 6.6 | 0.29 ± 0.13 |
| PTX-β-CD-NP | 298 ± 6 | 0.21 | −39.3 ± 5.2 | 63.3 ± 2.9 | 40.5 ± 5.12 |
| PTX-OH-β-CD-NP | 307 ± 7 | 0.24 | −42.1 ± 1.4 | 68.6 ± 4.4 | 171.01 ± 13.41 |
| PTX-NH-β-CD-NP | 310 ± 6 | 0.18 | −34.5 ± 3.9 | 59.5 ± 4.6 | 99.26 ± 10.13 |

The results show mean ± standard deviation (n =8).
PTX-NP: conventional PVM/MA nanoparticles with paclitaxel;
PTX-β-CD-NP: PVM/MA and β-CD nanoparticles with paclitaxel;
PTX-OH-β-CD-NP: PVM/MA and OH-β-CD nanoparticles with paclitaxel; and
PTX-NH-β-CD-NP: PVM/MA and NH-β-CD nanoparticles with paclitaxel.

Table 8 summarizes the main physicochemical characteristics of the nanoparticles assayed in the pharmacokinetic study. The control nanoparticles (PTX-NP) show a size close to 200 nm with a negative surface charge of −38 mV. In addition, the nanoparticles containing the encapsulated PTX-CD complex are significantly larger (close to 300 nm) and show a similar zeta potential in all the cases. Finally, it should be emphasized that the presence of the PTX-CD complex does not exert any effect on the manufacturing yield of the nanoparticles which varies between 50-60%.

The pharmacokinetic study was divided into three phases. In the first study, 10 mg/kg of the commercial paclitaxel formulation (Taxol®) were administered intravenously (i.v.) and orally to two groups of male Wistar rats (n=6). The second study consisted of orally administering solutions of paclitaxel (10 mg/kg) with (i) β-CD, (ii) OH-β-CD, or (iii) NH-β-CD, to groups of rats formed by 6 animals. Finally, for the pharmacokinetic study of the different formulations, the different formulations of nanoparticles (i) PTX-OH-β-CD-NP, (ii) PTX-β-CD-NP, (iii) PTX-NH-β-CD-NP, or (iv) PTX-NP were administered orally to different groups of animals. The selected dose of paclitaxel was 10 mg/kg.

After the administration, a volume of blood of approximately 300 μl was extracted at different times (0, 10, 30, 60, 90, 180, 360, 480 minutes, 24 and 30 hours), using EDTA as an anticoagulant and recovering the blood volume of the animal (rat) with an equivalent volume of physiological saline by an intraperitoneal (i.p.) route. The pharmacokinetic analysis of the results obtained after administering paclitaxel was carried out using the non-compartmental adjustment process of the WiNNonlin 1.5 pharmacokinetic adjustment program (Pharsight Corporation, Mountain View, United States).

Figure 8A:
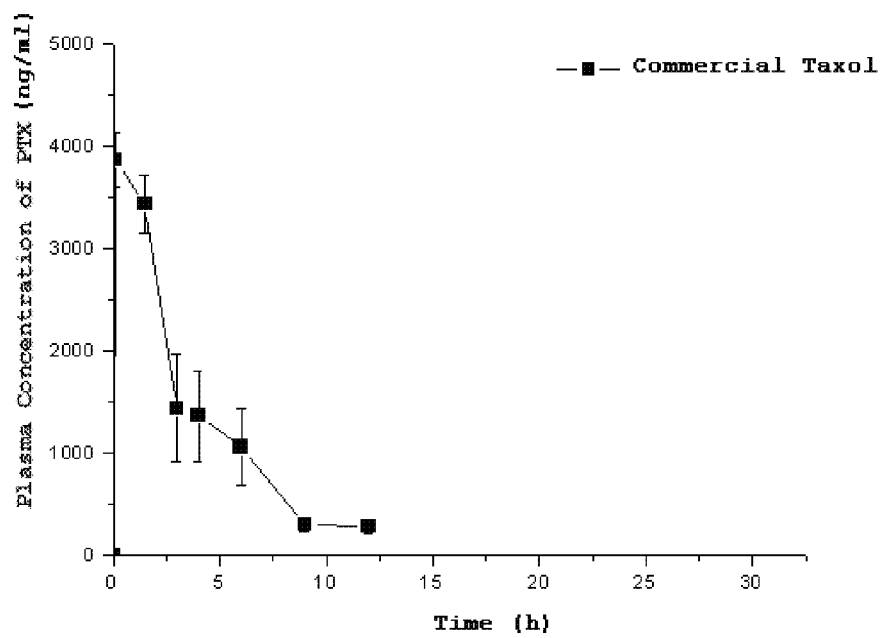
FIG. 8 is a set of graphs representing the plasma concentrations of paclitaxel (PTX) according to the time after the administration in laboratory animals of the different PTX formulations. The results show the mean±standard deviation. (A) Intravenous route, dose: 10 mg/kg. Taxol®: commercial paclitaxel formulation. (B) Oral route, dose: 10 mg/kg. Taxol®: commercial paclitaxel formulation; PTX-β-CD: β-CD complex with paclitaxel; PTX-OH-β-CD: OH-β-CD complex with paclitaxel; PTX-NH-β-CD: NH-β-CD complex with paclitaxel. (C) Oral route, dose: 10 mg/kg. PTX-NP: conventional PVM/MA nanoparticles with paclitaxel; PTX-β-CD-NP: PVM/MA and β-CD nanoparticles with paclitaxel; PTX-OH-β-CD-NP: PVM/MA and OH-β-CD nanoparticles with paclitaxel; PTX-NH-β-CD-NP: PVM/MA and NH-β-CD nanoparticles with paclitaxel; Taxol®: commercial formulation with paclitaxel. The values obtained for the commercial taxol formulation and PTX-NP overlap and appear on the X axis (Table 9).
Figure 8B:
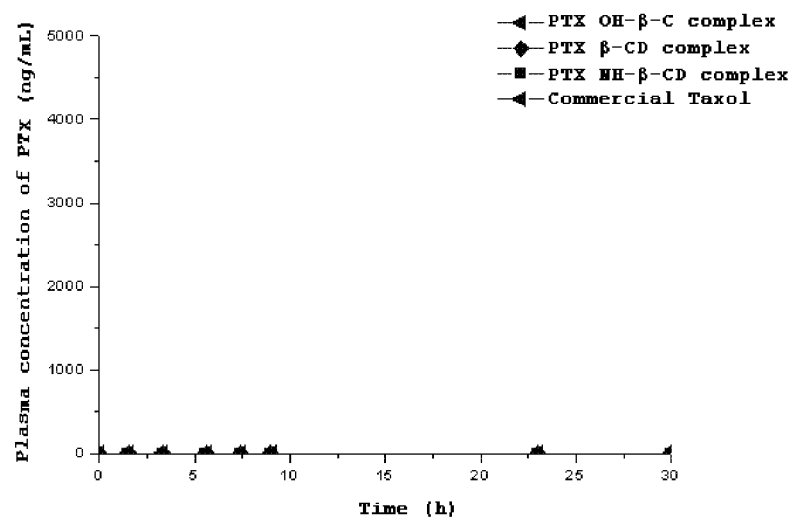
Figure 8C:
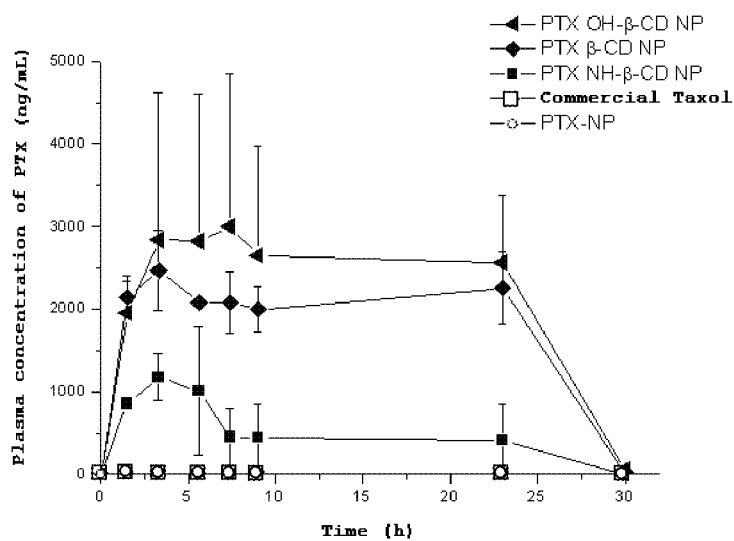

The obtained results are shown in FIG. 8. As can be observed, the i.v. administration of the conventional formulation (commercial taxol) shows a plasma concentration peak of paclitaxel in the first sample taking, followed by a two-phase decrease over time. Said profile is similar to that described by other authors (Yeh et al., Pharm Res 22(6): 867-74, 2005). When said commercial formulation was administered orally (FIG. 8B), the plasma levels of paclitaxel were nil. Similar results were obtained upon administering the PTX:CD complexes, none of them allowed detecting or quantifying significant levels of paclitaxel over time. On the contrary, when the paclitaxel formulations in nanoparticles containing cyclodextrins and paclitaxel were orally administered, it could be proved that these formulations give place to sustained plasma levels over time for at least 24 hours. In the time period comprised from 4 hours up to 24 hours after administering said nanoparticles, a plasma concentration plateau typical of the formulations which release the drug with 0 order kinetics could be observed for the three formulations. In any case, the PTX-β-CD-NP and PTX-OH-β-CD-NP formulations allow obtaining plasma levels that are considerably higher (3-4 times) than those obtained with the PTX-NH-β-CD-NP formulation. Also, it is interesting to emphasize that the administration of paclitaxel in conventional nanoparticles did not allow the absorption of the drug.

Table 9 shows the values of the pharmacokinetic parameters obtained after carrying out a non-compartmental analysis of the experimental data obtained after administering the different paclitaxel formulations in nanoparticles. As can be observed in said table, the value of AUC and MRT undergoes significant variations according to the type of cyclodextrin used in the formulation. In the case of oral PTX-OH-β-CD-NP and PTX-β-CD-NP formulations, similar values of AUC were obtained. In both oral formulations (PTX-OH-β-CD-NP and PTX-β-CD-NP) the maximum concentration reached is significantly higher than that reached in the remaining formulations in a time period of 6 and 5 hours, respectively. The mean residence time (MRT) of the drug in the organism was similar for the three formulations with cyclodextrins. These values were between 3 and 5 times higher than those reached after orally administering the commercial formulation (Taxol®).

Likewise, the elimination half-life of the drug in the terminal phase ($T_{1/2z}$) was similar for the formulations of nanoparticles containing cyclodextrin and paclitaxel, and, in any case, less than that obtained for the intravenously administered commercial formulation (Taxol®).

TABLE 9

Pharmacokinetic parameters of the different assayed formulations

| Formulation | Adm. Route | AUC (ng h/ml) | $C_{max}$ (ng) | $T_{max}$ (h) | MRT (h) | $T_{1/2z}$ ($h^{-1}$) | Cl/F (l/h) | Vss/F (L) |
|---|---|---|---|---|---|---|---|---|
| Taxol ® | i.v. | 11.126 | 2.541 | 0.22 | 3.00 | 3.71 | 0.23 | 0.68 |
| Taxol ® | Oral | 0 | 0 | 0 | 0 | 0 | 0 | 0 |
| PTX-OH-β-CD-NP | Oral | 67.127* | 5.679 | 6.17 | 11.09* | 1.32 | 0.05 | 0.51 |
| PTX-β-CD-NP | Oral | 65.965* | 3.171 | 4.90 | 13.72* | 1.48 | 0.04 | 0.59 |
| PTX-NH-β-CD-NP | Oral | 14.612 | 1.470 | 4.66 | 9.97* | 0.89 | 0.20 | 1.75 |
| PTX-NP | Oral | 0 | 0 | 0 | 0 | 0 | 0 | 0 |
| PTX-OH-β-CD Complex | Oral | 0 | 0 | 0 | 0 | 0 | 0 | 0 |
| PTX-β-CD Complex | Oral | 0 | 0 | 0 | 0 | 0 | 0 | 0 |

TABLE 9-continued

Pharmacokinetic parameters of the different assayed formulations

| Formulation | Adm. Route | AUC (ng h/ml) | $C_{max}$ (ng) | $T_{max}$ (h) | MRT (h) | $T_{1/2\,z}$ ($h^{-1}$) | Cl/F (l/h) | Vss/F (L) |
|---|---|---|---|---|---|---|---|---|
| PTX-NH-β-CD Complex | Oral | 0 | 0 | 0 | 0 | 0 | 0 | 0 |

*p < 0.05 PTX-OH β-CD-NP, PTX-β-CD-NP and PTX-NH β-CD-NP vs. commercial formulation (Taxol ®) Mann Whitney U Test.
$AUC_{0-inf}$: area under plasma level curve;
$C_{max}$: maximum conentration;
$T_{max}$: time at which $C_{max}$ is reached;
MRT: mean residence time;
$T_{1/2z}$: biological half-life in the terminal elimination phase
Cl/F: clearance (Cl = Dose × Bioavailability/AUC);
Vss: steady-state distribution volume (Vss = Dose × AUMC/$AUC^2$). The values of clearance and distribution volume are standardized against the value of the oral bioavailability of each formulation
PTX-OH-β-CD-NP: PVM/MA and OH-β-CD nanoparticles with paclitaxel;
PTX-β-CD-NP: PVM/MA and β-CD nanoparticles with paclitaxel;
PTX-NH-β-CD-NP: PVM/MA and NH-β-CD nanoparticles with paclitaxel; and
PTX-NP: conventional PVM/MA nanoparticles with paclitaxel.

The invention claimed is:

1. A nanoparticle formulated for oral delivery, the nanoparticle comprising:
    a complex comprising 2-hydroxypropyl-β-cyclodextrin and paclitaxel, wherein the paclitaxel is retained in a hydrophobic cavity of the 2-hydroxypropyl-β-cyclodextrin, and
    a methyl vinyl ether/maleic anhydride copolymer (PVM/MA) encapsulating the complex thereby forming the nanoparticle,
    wherein said nanoparticle prevents the action of a P-glycoprotein enzyme on the paclitaxel, and
    wherein the molar ratio paclitaxel/2-hydroxypropyl-β-cyclodextrin is between 1:1 and 1:2.

2. A pharmaceutical composition comprising the nanoparticle according to claim 1 and a pharmaceutically acceptable excipient, carrier or adjuvant.

3. A process for producing nanoparticles according to claim 1, comprising simultaneously incubating said methyl vinyl ether and maleic anhydride (PVM/MA) and a (2-hydroxypropyl-β-cyclodextrin):(paclitaxel) complex, ([CD:BAM complex]), in an organic solvent, and desolvating said PVM/MA with a hydroalcoholic solution.

4. A nanoparticle according to claim 1, where in the mean particle size of the nanoparticle is from about 200 nm to about 400 nm.

* * * * *